US010758886B2

(12) United States Patent
Woodbury et al.

(10) Patent No.: US 10,758,886 B2
(45) Date of Patent: Sep. 1, 2020

(54) CONDITIONED SURFACES FOR IN SITU MOLECULAR ARRAY SYNTHESIS

(71) Applicant: Arizona Board of Regents on behalf of Arizona State University, Scottsdale, AZ (US)

(72) Inventors: Neal Woodbury, Temple, AZ (US); Zhang-Gong Zhao, Tucson, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 15/264,426

(22) Filed: Sep. 13, 2016

(65) Prior Publication Data

US 2017/0106344 A1     Apr. 20, 2017

Related U.S. Application Data

(60) Provisional application No. 62/218,418, filed on Sep. 14, 2015.

(51) Int. Cl.
*B01J 19/00* (2006.01)
*C07K 1/04* (2006.01)
*C40B 50/18* (2006.01)
*C40B 80/00* (2006.01)

(52) U.S. Cl.
CPC .......... *B01J 19/0046* (2013.01); *C07K 1/047* (2013.01); *C40B 50/18* (2013.01); *C40B 80/00* (2013.01); *B01J 2219/00432* (2013.01); *B01J 2219/00596* (2013.01); *B01J 2219/00626* (2013.01); *B01J 2219/00659* (2013.01); *B01J 2219/00675* (2013.01); *B01J 2219/00725* (2013.01)

(58) Field of Classification Search
CPC ....... B01J 19/0046; C40B 80/00; C07K 1/047
See application file for complete search history.

(56) References Cited

U.S. PATENT DOCUMENTS

| | | |
|---|---|---|
| 5,143,854 A | 9/1992 | Pirrung et al. |
| 5,384,261 A | 1/1995 | Winkler et al. |
| 5,424,186 A | 6/1995 | Fodor et al. |
| 5,571,639 A | 11/1996 | Hubbell et al. |
| 5,593,839 A | 1/1997 | Hubbell et al. |
| 5,595,915 A | 1/1997 | Geysen |
| 5,677,195 A | 10/1997 | Winkler et al. |
| 5,919,523 A | 7/1999 | Sundberg et al. |
| 6,083,763 A | 7/2000 | Balch |
| 6,153,743 A | 11/2000 | Hubbell et al. |
| 6,309,831 B1 | 10/2001 | Goldberg et al. |
| 6,329,209 B1 | 12/2001 | Wagner et al. |
| 6,346,413 B1 | 2/2002 | Fodor et al. |
| 6,346,423 B1 | 2/2002 | Schembri |
| 6,359,125 B1 | 3/2002 | Kim et al. |
| 6,365,418 B1 | 4/2002 | Wagner et al. |
| 6,387,631 B1 | 5/2002 | Arnold et al. |
| 6,399,365 B2 | 6/2002 | Besemer et al. |
| 6,465,183 B2 | 10/2002 | Wolber |
| 6,475,808 B1 | 11/2002 | Wagner et al. |
| 6,475,809 B1 | 11/2002 | Wagner et al. |
| 6,489,159 B1 | 12/2002 | Chenchik et al. |
| 6,496,309 B1 | 12/2002 | Bliton et al. |
| 6,511,277 B1 | 1/2003 | Norris et al. |
| 6,545,748 B1 | 4/2003 | Trozera |
| 6,567,163 B1 | 5/2003 | Sandstrom |
| 6,569,671 B1 | 5/2003 | Okamoto et al. |
| 6,573,369 B2 | 6/2003 | Henderson et al. |
| 6,604,902 B2 | 8/2003 | Norris et al. |
| 6,620,584 B1 | 9/2003 | Chee et al. |
| 6,630,358 B1 | 10/2003 | Wagner et al. |
| 6,660,479 B2 | 12/2003 | Kim et al. |
| 6,706,875 B1 | 3/2004 | Goldberg et al. |
| 6,723,517 B1 | 4/2004 | Bamdad |
| 6,733,977 B2 | 5/2004 | Besemer et al. |
| 6,780,582 B1 | 8/2004 | Wagner et al. |
| 6,800,449 B1 * | 10/2004 | Haynes ................. G01N 33/66 435/7.1 |
| 6,806,954 B2 | 10/2004 | Sandstrom |
| 6,824,669 B1 | 11/2004 | Li et al. |
| 6,877,665 B2 | 4/2005 | Challa et al. |
| 6,890,760 B1 | 5/2005 | Webb |
| 6,897,073 B2 | 5/2005 | Wagner et al. |
| 6,919,181 B2 | 7/2005 | Hargreaves |
| 6,989,267 B2 | 1/2006 | Kim et al. |
| 6,989,276 B2 | 1/2006 | Thompson et al. |
| 7,006,680 B2 | 2/2006 | Gulati |

(Continued)

FOREIGN PATENT DOCUMENTS

| | | |
|---|---|---|
| CN | 1659287 A | 8/2005 |
| CN | 101389769 A | 3/2009 |

(Continued)

OTHER PUBLICATIONS

Tjong, masters thesis, Immobilization Strategies for Peptide Microarrays, 2012, pp. 1-47 (Year: 2012).*

(Continued)

*Primary Examiner* — Narayan K Bhat
(74) *Attorney, Agent, or Firm* — Byrne Poh LLP; Nina R. Horan

(57) ABSTRACT

Described herein are in situ synthesized arrays and methods of making them, wherein array signal sensitivity and robustness is enhanced by carrying out conditioning steps and/or generating linkers during synthesis. An array comprises a surface with a collection of features, wherein the features comprise molecules or polymers attached to the surface. In certain embodiments of the invention, carrying out conditioning steps during array synthesis can yield arrays with improved signal. In other embodiments, linkers are synthesized on the array surface prior to synthesis of functional molecules, wherein increasing linker length can correspond to an improvement in the signal generated by the array.

8 Claims, 5 Drawing Sheets
(1 of 5 Drawing Sheet(s) Filed in Color)
Specification includes a Sequence Listing.

(56) References Cited

U.S. PATENT DOCUMENTS

| | | | |
|---|---|---|---|
| 7,081,954 | B2 | 7/2006 | Sandstrom |
| 7,108,472 | B2 | 9/2006 | Norris et al. |
| 7,130,458 | B2 | 10/2006 | Bartell |
| 7,148,058 | B2 | 12/2006 | Charych et al. |
| 7,247,469 | B2 | 7/2007 | Wagner et al. |
| 7,354,721 | B2 | 4/2008 | Tchaga |
| 7,466,851 | B2 | 12/2008 | Gulati |
| 7,522,271 | B2 | 4/2009 | Sandstrom |
| 7,534,563 | B2 | 5/2009 | Hargreaves |
| 7,569,343 | B2 | 8/2009 | Marton et al. |
| 7,588,906 | B2 | 9/2009 | Brueggemeier et al. |
| 7,622,295 | B2 | 11/2009 | Cabezas |
| 7,682,797 | B2 | 3/2010 | Thompson et al. |
| 7,682,798 | B2 | 3/2010 | Thompson et al. |
| 7,695,919 | B2 | 4/2010 | Apel et al. |
| 7,723,125 | B2 | 5/2010 | Tchaga |
| 7,993,583 | B2 | 8/2011 | Dugan et al. |
| 8,073,626 | B2 | 12/2011 | Troup et al. |
| 8,148,141 | B2 | 4/2012 | Nokihara et al. |
| 8,242,058 | B2 | 8/2012 | Raines et al. |
| RE44,031 | E | 2/2013 | Apel et al. |
| 9,212,225 | B1* | 12/2015 | Ellwanger ............ C07K 16/2803 |
| 2003/0082579 | A1 | 5/2003 | Felgner et al. |
| 2003/0207467 | A1 | 11/2003 | Snyder et al. |
| 2004/0038307 | A1 | 2/2004 | Lee et al. |
| 2004/0038556 | A1 | 2/2004 | French et al. |
| 2004/0048311 | A1 | 3/2004 | Ault-Riche et al. |
| 2004/0063902 | A1 | 4/2004 | Miranda |
| 2004/0071705 | A1 | 4/2004 | Sato et al. |
| 2004/0241748 | A1* | 12/2004 | Ault-Riche ...... G01N 33/54353 435/7.1 |
| 2005/0009204 | A1 | 1/2005 | Fang et al. |
| 2005/0048566 | A1 | 3/2005 | Delisi et al. |
| 2005/0064395 | A1 | 3/2005 | Israel et al. |
| 2005/0255491 | A1 | 11/2005 | Lee et al. |
| 2006/0052948 | A1 | 3/2006 | Gorlach |
| 2007/0003954 | A1 | 1/2007 | Kodadek |
| 2007/0015172 | A1 | 1/2007 | Zhang et al. |
| 2007/0020678 | A1 | 1/2007 | Ault-Riche et al. |
| 2007/0099256 | A1 | 5/2007 | Sundararajan et al. |
| 2007/0122841 | A1 | 5/2007 | Rajasekaran et al. |
| 2007/0122842 | A1 | 5/2007 | Rajasekaran et al. |
| 2008/0124719 | A1 | 5/2008 | Chung et al. |
| 2008/0193965 | A1 | 8/2008 | Zeng et al. |
| 2009/0075828 | A1 | 3/2009 | Fisher et al. |
| 2009/0131278 | A1 | 5/2009 | Wagner et al. |
| 2009/0176664 | A1 | 7/2009 | Chu |
| 2009/0258796 | A1 | 10/2009 | Rajasekaran et al. |
| 2010/0035765 | A1 | 2/2010 | Kodadek |
| 2010/0137155 | A1* | 6/2010 | Akagi .............. G01N 33/54353 506/9 |
| 2010/0221212 | A1* | 9/2010 | Stagliano ........... G01N 33/6866 424/85.4 |
| 2010/0261205 | A1 | 10/2010 | Kakuta et al. |
| 2011/0046015 | A1 | 2/2011 | Honda et al. |
| 2011/0065594 | A1 | 3/2011 | Thompson et al. |
| 2011/0105366 | A1 | 5/2011 | Lebl et al. |
| 2011/0143953 | A1 | 6/2011 | Johnston et al. |
| 2011/0190149 | A1 | 8/2011 | Tainsky et al. |
| 2011/0275537 | A1 | 11/2011 | Rychlewski et al. |
| 2011/0301057 | A1 | 12/2011 | Propheter et al. |
| 2011/0301058 | A1 | 12/2011 | Cheng et al. |
| 2012/0149061 | A1* | 6/2012 | Stagliano ........... A61K 47/6845 435/69.6 |
| 2012/0189702 | A1 | 7/2012 | Gupta |
| 2012/0190574 | A1 | 7/2012 | Johnston et al. |
| 2012/0238477 | A1 | 9/2012 | Albert et al. |
| 2013/0338044 | A1* | 12/2013 | Liao ................ G01N 33/54353 506/32 |
| 2014/0087963 | A1 | 3/2014 | Johnston et al. |
| 2015/0141296 | A1 | 5/2015 | Woodbury et al. |
| 2015/0217258 | A1 | 8/2015 | Woodbury et al. |

FOREIGN PATENT DOCUMENTS

| | | |
|---|---|---|
| CN | 102164957 A | 8/2011 |
| EP | 0476014 B1 | 8/1994 |
| EP | 0728520 A1 | 8/1996 |
| EP | 1785726 A1 | 5/2007 |
| WO | WO-9015070 A1 | 12/1990 |
| WO | WO-9118980 A1 | 12/1991 |
| WO | WO-9306121 A1 | 4/1993 |
| WO | WO-9408051 A1 | 4/1994 |
| WO | WO-9512608 A1 | 5/1995 |
| WO | WO-9530642 A1 | 11/1995 |
| WO | WO-9535503 A1 | 12/1995 |
| WO | WO-9609668 A1 | 3/1996 |
| WO | WO-9727329 A1 | 7/1997 |
| WO | WO-0004382 A1 | 1/2000 |
| WO | WO-02097051 A2 | 12/2002 |
| WO | WO-03019192 A1 | 3/2003 |
| WO | WO-2005050224 A2 | 6/2005 |
| WO | WO-2007147141 A2 | 12/2007 |
| WO | WO-2008048970 A2 | 4/2008 |
| WO | WO-2008085185 A2 | 7/2008 |
| WO | WO-2008151146 A2 | 12/2008 |
| WO | WO-2009140039 A2 | 11/2009 |
| WO | WO-2010148365 A2 | 12/2010 |
| WO | WO-2011109440 A1 | 9/2011 |
| WO | WO-2011150168 A1 | 12/2011 |
| WO | WO-2013063133 A1 | 5/2013 |
| WO | WO-2014062981 A1 | 4/2014 |
| WO | WO-2014036312 A3 | 5/2015 |

OTHER PUBLICATIONS

Wang et al, Selective protein-peptide interactions at surfaces, 2014, Acta Biomaterialia, 10, 761-768. (Year: 2013).*

Wang, Thesis, Exploring the Nature of Protein-Peptide Interactions on Surfaces, 2014, pp., 1-164 (Year: 2014).*

Shen L, Hansen DT, Johnston SA, Legutki JB (2014) Could immune signatures technology enable the development of a preventative cancer vaccine? Expert Rev Vaccines 13: 577-579.

Legutki JB, Johnston SA (2013) Immuno signatures can predict vaccine efficacy. Proceedings of the National Academy of Sciences of the United States of America 110: 18614-18619.

McGuire MJ, Johnston SA, Sykes KF (2012) Novel immune-modulator identified by a rapid, functional screen of the parapoxvirus ovis (Orf virus) genome. Proteome Science 10.

Navalkar KA, Johnston SA, Woodbury N, Galgiani JN, Magee DM, et al. (2014) Application of immune signatures for diagnosis of valley Fever. Clin Vaccine Immunol 21: 1169-1177.

Restrepo L, Stafford P, Johnston SA (2013) Feasibility of an early Alzheimer's disease immunosignature diagnostic test. Journal of Neuroimmunology 254: 154-160.

Richer J, Johnston SA, Stafford P (2014) Epitope identification from fixed-complexity random-sequence peptide microarrays. Molecular & Cellular Proteomics 14.

Scheck AC, Stafford P, Hughes A, Cichacz Z, Coons SW, et al. (2012) Immunosignaturing for the Diagnosis and Characterization of Human Brain Tumors. Neuro-Oncology 14: 100-100.

Sykes KF, Legutki JB, Stafford P. Immunosignaturing: a critical review (2013) Trends in Biotechnology 31: 45-51.

Agarwal, et al. Disregulated expression of the Th2 cytokine gene in patients with intraoral squamous cell carcinoma. Immunol Invest. Feb. 2003;32(1-2):17-30.

Anderson, et al. The human plasma proteome: history, character, and diagnostic prospects. Mol Cell Proteomics. Nov. 2002;1(11):845-67.

Andresen et al., Deciphering The Antibodyome Peptide Arrays for Serum Antibody Biomarker Diagnostics, Current Proteomics, 6;1-12 (2009).

Bailey. Meme: discovering and analyzing DNA and protein sequence motifs. (2006) Nucleic Acids Res. 34(suppl 2): W369-W373.

Bauer et al., Identification and Quantification of a New Family of Peptide Endocannabinoids (Pepcans) Showing Negative Allosteric Modulation at CB1 Receptors, Journal of Biological Chemistry (2012) 287(44); 36944-36967.

(56) References Cited

OTHER PUBLICATIONS

Berglund, et al. A Genecentric Human Protein Atlas for Express Profiles Based on antibodies. Oct. 1, 2008, Molecular and Cellular Proteomics, 7, pp. 2019-2027.
Betanzos, C., et al. Bacterial glycoprofiling by using random sequence peptide microarrays. (2009) ChemBioChem vol. 10, pp. 877-888.
Boltz, et al. Peptide microarrays for carbohydrate recognition. Analyst. Apr. 2009;134(4):650-2. doi: 10.1039/b823156g. Epub Feb 11, 2009.
Borrebaeck. Antibodies in diagnostics—from immunoassays to protein chips. Immunol Today. Aug. 2000;21(8):379-82.
Breitling F. et al. High-density peptide arrays. Mol. BioSyst., vol. 5, pp. 224-234, 2009.
Brown, et al. Statistical methods for analyzing immunosignatures. BMC Bioinformatics. Aug. 19, 2011;12:349. doi: 10.1186/1471-2105-12-349.
Brown, et al. The preclinical natural history of serous ovarian cancer: defining the target for early detection. PLoS Med. Jul. 2009;6(7):e1000114. doi: 10.1371/journal.pmed.1000114. Epub Jul. 28, 2009.
Brusic, et al. Information technologies for vaccine research. Expert Rev Vaccines. Jun. 2005;4(3):407-17.
Butler, et al. The immunochemistry of sandwich ELISAs-VI. Greater than 90% of monoclonal and 75% of polyclonal anti-fluorescyl capture antibodies (CAbs) are denatured by passive adsorption. Mol Immunol. Sep. 1993;30(13):1165-75.
Butler. Solid supports in enzyme-linked immunosorbent assay and other solid-phase immunoassays. Methods. Sep. 2000;22(1):4-23.
Casey, et al. Phage display of peptides in ligand selection for use in affinity chromatography. Methods Mol Biol. 2008;421:111-24.
Cenci, et al. Managing and exploiting stress in the antibody factory. FEBS Lett. Jul. 31, 2007;581(19):3652-7. Epub Apr. 24, 2007.
Cerecedo, et al. Mapping of the IgE and IgG4 sequential epitopes of milk allergens with a peptide microarray-based immunoassay. J Allergy Clin Immunol. Sep. 2008;122(3):589-94. doi: 10.1016/j.jaci.2008.06.040.
Chase, et al. Evaluation of biological sample preparation for immunosignature-based diagnostics. Clin Vaccine Immunol. Mar. 2012;19(3):352-8. doi: 10.1128/CVI.05667-11. Epub Jan 11, 2012.
Chen, et al. Identification of multiple cancer/testis antigens by allogeneic antibody screening of a melanoma cell line library. Proc Natl Acad Sci U S A. Jun. 9, 1998;95(12):6919-23.
Chen, G. et al. Autoantibody Profiles Reveal Ubiquilin 1 as a Humoral Immune Response Target in Lung Adenocarcinoma. Cancer Res. vol. 67, No. 7 (Apr. 1, 2007).
Chene, P., Challenges in Design of Biochemical Assays for the Identification of Small Molecules to Target Multiple Conformations of Protein Kinases. Drug Discovery Today, 13(11/12); 522-529 (2008).
Christian, R.B., et al. (1992) Simplified methods for construction, assessment and rapid screening of peptide libraries in bacteriophage. Journal of Molecular Biology 227, 711-718.
Cooperman, et al. Cell division rates of primary human precursor B cells in culture reflect in vivo rates. Stem Cells. 2004;22(6):1111-20.
Cretich, et al. Epitope mapping of human chromogranin A by peptide microarrays. Methods Mol Biol. 2009;570:221-32. doi: 10.1007/978-1-60327-394-7_10.
Cretich. Protein and peptide arrays: Recent trends and new directions. (2006) Biomol. Eng. 23: 77-88 (2006).
Daver, et al. The usefulness of prostate-specific antigen and prostatic acid phosphatase in clinical practice. Am J Clin Oncol. 1988;11 Suppl 2:S53-60.
Derda, et al. Diversity of phage-displayed libraries of peptides during panning and amplification. Molecules. Feb. 21, 2011;16(2):1776-803. doi: 10.3390/molecules16021776.
Diehnelt, et al. Discovery of high-affinity protein binding ligands—backwards. PLoS One. May 19, 2010;5(5):e10728. doi: 10.1371/journal.pone.0010728.

Draghici. Statistics and Data Analysis for Microarrays Using R and Bioconductor. Chapman & Hall/CRC. 2012.
Engvall, et al. Enzyme-linked immunosorbent assay (ELISA). Quantitative assay of immunoglobulin G. Immunochemistry. Sep. 1971;8(9):871-4.
EP 10790305.6 Extended European Search Report dated Aug. 20, 2013.
European Application No. 13834985.7 Search Report dated Apr. 13, 2016.
European Patent Application No. 13 833992.4 European Search Report dated Apr. 25, 2016.
Falsey, J.R., et al. Peptide and small molecule microarray for high throughput cell adhesion and functional assays. Bioconjugate Chem. (2001) 12, 346-353.
Fodor et al., Light-directed, spatially addressable parallel chemical synthesis, Science, Feb. 1991, 767-73, vol. 251, No. 4995.
Fodor. Multiplexed biochemical assays with biological chips. (1993) Nature 364: 555-556.
Folgori, A., et al. A general strategy to identify mimotopes of pathological antigens using only random peptide libraries and human sera. (1994) EMBO Journal, vol. 13, No. 9, pp. 2236-2243.
Foong, et al. Bacterial glycoprofiling by using random sequence peptide microarrays. Chembiochem. Mar. 23, 2009;10(5):877-88. doi: 10.1002/cbic.200800716.
Foong, et al. Current advances in peptide and small molecule microarray technologies. Curr Opin Chem Biol. Apr. 2012;16(1-2):234-42. doi: 10.1016/j.cbpa.2011.12.007. Epub Jan. 3, 2012.
Forster, et al. The bulk of the peripheral B-cell pool in mice is stable and not rapidly renewed from the bone marrow. Proc Natl Acad Sci U S A. Jun. 1990;87(12):4781-4.
Frith. Discovering Sequence Motifs with Arbitrary Insertions and Deletions. (2008) PLOS Comput. Blol. 4: e1000071.
Fu et al., Exploring peptide space for enzyme modulators, J. Am. Chem. Soc., Apr. 2010, 6419-6424, vol. 132, No. 18.
Fu et al., Interenzyme substrate diffusion for an enzyme cascade organized on spatially addressable DNA nanostructures, J Am Chem Soc., Mar. 2012, 5516-9, vol. 134, No. 12.
Fu, et al. Peptide-modified surfaces for enzyme immobilization. PLoS One. Apr. 8, 2011;6(4):e18692. doi: 10.1371/journal.pone.0018692.
Gallina, et al. Prediction of pathological stage is inaccurate in men with PSA values above 20 ng/mL. Eur Urol. Nov. 2007;52(5):1374-80. Epub Dec. 11, 2006.
Geysen, et al. Use of peptide synthesis to probe viral antigens for epitopes to a resolution of a single amino acid. Proc Natl Acad Sci U S A. Jul. 1984;81(13):3998-4002.
Greving et al., Feature-level MALDI-MS characterization of in situ-synthesized peptide microarrays, Langmuir, Feb. 2009, 1456-1459, vol. 26, No. 3.
Greving, et al. High-throughput screening in two dimensions: binding intensity and off-rate on a peptide microarray. Anal Biochem. Jul. 1, 2010;402(1):93-5. doi: 10.1016/j.ab.2010.03.002. Epub Mar. 6, 2010.
Greving, et al. Thermodynamic additivity of sequence variations: an algorithm for creating high affinity peptides without large libraries or structural information. PLoS One. Nov. 11, 2010;5(11):e15432. doi: 10.1371/journal.pone.0015432.
Gupta, N., et al. Engineering a synthetic ligand for tumor necrosis factor-alpha.(2011) Bioconjugate Chemistry, vol. 22, pp. 1473-1478.
Halperin, R.F., et al., GuiTope: an application for mapping random-sequence peptides to protein sequences. (2012) BMC Bioinformatics vol. 13, No. 1.
Halperin, R.F., Stafford, P. and Johnson S.A. Exploring Antibody Recognition of Sequence Space through Random-Sequence Peptide Microarrays. (2011) Molecular Cell Proteomics, vol. 10, No. 3, pp. 1-10.
Han et al., DNA origami with complex curvatures in three-dimensional space, Science, Apr. 2011, 342-346, vol. 332, No. 6027.
Hanash, S. Disease proteomics. (Mar. 2003) Nature vol. 422, pp. 226-232.

(56) References Cited

OTHER PUBLICATIONS

Hao, et al. Homeostasis of peripheral B cells in the absence of B cell influx from the bone marrow. J Exp Med. Oct. 15, 2001;194(8):1151-64.
Hecker, M. et al. Computational analysis of high-density peptide microarray datga with application from systemic sclerosis to multiple sclerosis. Autoimmunity Reviews, vol. 11; pp. 180-190 (2012).
Hori, et al. Mathematical model identifies blood biomarker-based early cancer detection strategies and limitations. Sci Transl Med. Nov. 16, 2011;3(109):109ra116. doi: 10.1126/scitranslmed.3003110.
Huang, et al. MIMOX: a web tool for phage display based epitope mapping. BMC Bioinformatics. Oct. 12, 2006;7:451.
Hughes, et al. Immunosignaturing can detect products from molecular markers in brain cancer. PLoS One. 2012;7(7):e40201. doi: 10.1371/journal.pone.0040201. Epub Jul. 16, 2012.
International search report and written opinion dated Oct. 22, 2012 for PCT/US2012/036631.
International search report and written opinion dated Dec. 17, 2013 for PCT Application No. US2013/058325.
International search report and written opinion dated Feb. 3, 2014 for PCT/US2013/057373.
International search report and Written opinion dated Apr. 28, 2015 for PCT/US2013/057373.
International search report dated Dec. 20, 2013 for PCT/US2013/065541.
Jagger, B.W. et al., An Overlapping Protein-Coding Region in Influenza A Virus Segment 3 Modulates the Host Response. Science 337:199-204 (Jul. 13, 2012).
Jonassen. Efficient discovery of conserved patterns using a pattern graph. (1997) Comput. Appl. Biosci. 13: 509-22.
Ke et al., Self-assembled water-soluble nucleic acid probe tiles for label-free RNA hybridization assays, Science, Jan. 2008, 180-183, vol. 319, No. 5860.
Kroening, et al. Autoreactive antibodies raised by self derived de novo peptides can identify unrelated antigens on protein microarrays. Are autoantibodies really autoantibodies? Exp Mol Pathol. Jun. 2012;92(3):304-11. doi: 10.1016/j.yexmp.2012.03.002. Epub Mar. 8, 2012.
Kukreja, et al. Comparative study of classification algorithms for immunosignaturing data. BMC Bioinformatics. Jun. 21, 2012;13:139. doi: 10.1186/1471-2105-13-139.
Kukreja, M., et al. Immunosignaturing Microarrays Distinguish Antibody Profiles of Related Pancreatic Diseases. (2012) Journal of Proteomics & Bioinformatics, vol. S6, pp. 001.
Legutki, et al. A general method for characterization of humoral immunity induced by a vaccine or infection. Vaccine. Jun. 17, 2010;28(28):4529-37. doi: 10.1016/j.vaccine.2010.04.061. Epub May 5, 2010.
Legutki et al., Scalable high-density peptide arrays for comprehensive health monitoring., Nature Communications, Sep. 2014, 5:4785(7 pages).
Legutki, J.B., et al. Scalable high-density peptide arrays for comprehensive health monitoring. Nature Communications, vol. 5, p. 4785; (Sep. 3, 2014).
Lewczuk, et al. Amyloid beta peptides in plasma in early diagnosis of Alzheimer's disease: A multicenter study with multiplexing. Exp Neurol. Jun. 2010;223(2):366-70. doi: 10.1016/j.expneurol.2009.07.024. Epub Aug. 5, 2009.
Lin, et al. Development of a novel peptide microarray for large-scale epitope mapping of food allergens. J Allergy Clin Immunol. Aug. 2009;124(2):315-22, 322.e1-3. doi: 10.1016/j.jaci.2009.05.024. Epub Jul. 3, 2009.
Liu et al. Towards proteome-wide production of monoclonal antibody by phage display. J Mol Biol. 315(5):1063-1073 (2002).
Liu, R., et al. Combinatorial peptide library methods for immunobiology research. (2003) Experimental Hematology vol. 31, pp. 11-30.
Lorenz, P., et al. Probing the epitope signatures of IgG antibodies in human serum from patients with autoimmune disease. (2009) Methods in Molecular Biology, Epitope Mapping Protocls, vol. 524, pp. 247-258.
Lund, et al., Molecular robots guided by prescriptive landscapes, Nature, May 2010, 206-210, vol. 465, No. 7295.
Mackey, et al. Getting more from less: algorithms for rapid protein identification with multiple short peptide sequences. Mol Cell Proteomics. Feb. 2002;1(2):139-47.
Merbl, et al. A Systems Immunology Approach to the Host-Tumor Interaction: Large-Scale Patterns of Natural Autoantibodies Distinguish Healthy and Tumor-Bearing Mice. PLoS One vol. 4, Issue 6, p. e6053. Jun. 2009.
Mestas, et al., Of Mice and Not Men: Differences Between Mouse and Human Immunology, The Journal of Immunology, 172;2731-2738 (2004).
Min et al. Peptide arrays: towards routine implementation. Current Opinion in Chemical Biology vol. 8, pp. 554-558, 2004.
Miseta, Attila et al. Relationship Between the Occurrence of Cysteine in Proteins and the Complexity of Organisms. (2000) Mol. Biol. Evol., vol. 17, pp. 1232-1239.
Mohan, S., et al. Association energetics of cross-reactive and specific antibodies. (Feb. 17, 2009) Biochemistry vol. 48, No. 6, pp. 1390-1398.
Moller, et al. DNA probes on chip surfaces studied by scanning force microscopy using specific binding of colloidal gold. Nucleic Acids Res. Oct. 15, 2000;28(20):E91.
Moreau, et al. Discontinuous epitope prediction based on mimotope analysis. Bioinformatics. May 1, 2006;22(9):1088-95. Epub Jan. 24, 2006.
Navalkar, K.A. et al. Peptide based diagnostics: Are random-sequence peptides more useful than tiling proteome sequences? Journal of Immunological Methods, vol. 417, pp. 10-21 (2015).
Neuman De Vegvar, et al. Microarray profiling of antiviral antibodies for the development of diagnostics, vaccines, and therapeutics. (2004) Clinical Immunology, vol. 111 pp. 196-201.
Nobrega, A., et al. Functional diversity and clonal frequencies of reactivity in the available antibody repertoire. (1998) European Journal of Immunology vol. 28, pp. 1204-1215.
Northen et al., Combinatorial screening of biomimetic protein affinity materials, Adv Mater., Oct. 2008, 4691-4697, vol. 20, No. 24.
Office action dated Apr. 8, 2013 for U.S. Appl. No. 13/379,080.
Office action dated Sep. 12, 2014 for U.S. Appl. No. 13/379,080.
Office action dated Sep. 20, 2013 for U.S. Appl. No. 13/624,332.
Office action dated Sep. 20, 2013 for U.S. Appl. No. 13/624,386.
Office action dated Oct. 3, 2013 for U.S. Appl. No. 13/379,080.
Panicker, R.C., et al. Recent advances in peptide-based microarray technologies. (2004) Combinatorial Chemistry & High Throughput Screening vol. 7, pp. 547-556.
PCT/US2013/058325 International Preliminary Report on Patentability dated Mar. 10, 2015.
Perez-Gordo, et al. Epitope mapping of Atlantic salmon major allergen by peptide microarray immunoassay. Int Arch Allergy Immunol. 2012;157(1):31-40. doi: 10.1159/000324677. Epub Sep. 5, 2011.
Price et al., On silico peptide microarrays for high-resolution mapping of antibody epitopes and diverse protein-protein interactions, Nat Med, Sep. 2012, 1434-40, vol. 18, No. 9.
Quackenbush, et al. Computational Analysis of Microarray Data, Nature Reviews, 2;418-427 (2001).
Quiintana, et al., Antigen-chip technology for accessing global information about the state of the body. 2006 Lupus vol. 15, pp. 428-430.
Quintana, et al. The Natural autoantibody repertoire and autoimmune disease. Biomedicine & Pharmacotheraphy vol. 58 (2004) pp. 276-281.
Reddy, et al. Identification of candidate IgG biomarkers for Alzheimer's disease via combinatorial library screening. Cell. Jan. 7, 2011;144(1):132-42. doi: 10.1016/j.cell.2010.11.054.
Reddy, et al., Protein fingerprinting in complex mixtures with peptoid microarrays. Proc. of the Nat'l Academy of Sciences, Nat'l Academy of Sciences, US, 102(36):12672-12677 Sep. 2005.

(56) References Cited

OTHER PUBLICATIONS

Reineke, et al., Epitope Mapping Protocols, Method in Molecular Biology 524, 2nd Edition, Huma Press. 1-447 (2009).
Reineke, et al. Identification of Distinct Antibody Epitopes and mimotopes from a peptide array of 5520 randomly generated sequences. Journal of Immunological Methods vol. 267 (2002) pp. 37-51.
Restrepo, et al. Application of immunosignatures to the assessment of Alzheimer's disease. Ann Neurol. Aug. 2011;70(2):286-95. doi: 10.1002/ana.22405.
Rigoutsos. Combinatorial pattern discovery in biological sequences: the TEIRESIAS algorithm. (1998) Bioinformatics vol. 14, No. 1, pp. 55-67.
Rigoutsos. In Silico Pattern-Based Analysis of the Human Cytomegalovirus Genome. (1998) Bioinformatics 14: 55-67.
Roobol. Contemporary role of prostate cancer gene 3 in the management of prostate cancer. Curr Opin Urol. May 2011;21(3):225-9. doi: 10.1097/MOU.0b013e328344939c.
Shan et al., Imaging local electrochemical current via surface plasmon resonance, Science, Mar. 2010, 1363-66, vol. 327, No. 5871.
Sharma et al., Control of self-assembly of DNA tubules through integration of gold nanoparticles, Science, Jan. 2009, 112-116, vol. 323, No. 5910.
Shreffler, W.G., et al. IgE and IgG4 epitope mapping by microarray immunoassay reveals the diversity of immune response to the peanut allergen, Ara h 2. (2005) J Allergy Clin Immunol vol. 116, No. 4, pp. 893-899.
Singh-Gasson et al., Maskless fabrication of light-directed oligonucleotide microarrays using a digital micromirror array, Nat Biotechnol, Oct. 1999, 974-978, vol. 17, No. 10.
Stafford, et al. Physical characterization of the immunosignaturing effect. Mol Cell Proteomics. Apr. 2012;11(4):M111.011593. doi: 10.1074/mcp.M111.011593. Epub Jan. 18, 2012.
Stafford P, and Johnston,Microarray technology displays the complexities of the humoral immune response. Expert Rev. Mol. Diagn. vol. 11, No. 1, pp. 5-8, Jan. 2011.
Stafford, P., et al Immunosignature system for diagnosis of cancer. PNAS, vol. 111, No. 30; pp. E3072-E3080 (Jul. 14, 2014).
Sulzer, et al. Memory in idiotypic networks due to competition between proliferation and differentiation. Bull Math Biol. Nov. 1993;55(6):1133-82.
Szardenings, M. Phage display of random peptide libraries: applications, limits, and potential. (2003) Journal of Receptors and Signal Transduction, vol. 23, No. 4, pp. 307-349.
Takulapalli et al., Electrical detection of amine ligation to a metalloporphyrin via a hybrid SOI-MOSFET, J. Am. Chem. Soc., Jan. 2008, 2226-2233, vol. 130, No. 7.
Tang et al., Current Developments in SELDI Affinity Technology, Mass Spectrometry Reviews 23;34-44 (2004).
Tedesco, et al. A new strategy for the early diagnosis of rheumatoid arthritis: a combined approach. Autoimmun Rev. Jan. 2009;8(3):233-7. doi: 10.1016/j.autrev.2008.07.031. Epub Aug. 15, 2008.
Thompson, et al. Prostate-specific antigen in the early detection of prostate cancer. CMAJ. Jun. 19, 2007;176(13):1853-8.
Thorpe, I.F., and Brooks, C.L., Molecular evolution of affinity and flexibility in the immune system. (May 22, 2007) PNAS vol. 104, No. 21, pp. 8821-8826.
Uhlen, M., et al. Generation and validation of affinity reagents on a proteome-wide level. (2009) Journal of Molecular Recognition, vol. 22, pp. 57-64.
United States Patent and Trademark Office, Subject Matter Eligibility Examples: Life Sciences, Subject Matter Eligibility Update, 2016, 1-31.
U.S. Appl. No. 13/379,080 Advisory Action dated Mar. 4, 2014.
U.S. Appl. No. 13/379,080 Final Office action dated Apr. 8, 2013.
U.S. Appl. No. 13/379,080 Final Office action dated Oct. 3, 2013.
U.S. Appl. No. 13/379,080 Final Office action dated Sep. 12, 2014.
U.S. Appl. No. 13/379,080 Office Action dated Aug. 4, 2016.
U.S. Appl. No. 13/379,080 Office action dated Oct. 11, 2012.
U.S. Appl. No. 13/379,080 Restriction Requirement dated Mar. 29, 2016.
U.S. Appl. No. 13/624,332 Advisory Action dated Mar. 4, 2014.
U.S. Appl. No. 13/624,332 Final action dated Sep. 20, 2013.
U.S. Appl. No. 13/624,332 Office Action dated Feb. 8, 2016.
U.S. Appl. No. 13/624,332 Office action dated Jan. 22, 2013.
U.S. Appl. No. 13/624,332 Office Action dated Jul. 18, 2016.
U.S. Appl. No. 13/624,386 Advisory Action dated Mar. 4, 2014.
U.S. Appl. No. 13/624,386 Final action dated Sep. 20, 2013.
U.S. Appl. No. 13/624,386 Office action dated Jan. 23, 2013.
U.S. Appl. No. 13/624,386 Office Action dated Jan. 7, 2016.
U.S. Appl. No. 13/624,386 Office Action dated Jul. 25, 2016.
U.S. Appl. No. 13/683,778 Notice of Allowance dated Nov. 24, 2014.
U.S. Appl. No. 13/683,778 Office Action dated Oct. 1, 2013.
U.S. Appl. No. 14/014,168 Advisory Office Action dated Dec. 16, 2016.
U.S. Appl. No. 14/014,168 Office Action dated Jan. 6, 2016.
U.S. Appl. No. 14/014,168 Restriction Requirement dated Oct. 1, 2015.
U.S. Appl. No. 14/424,022 Office Action dated Jun. 1, 2016.
U.S. Appl. No. 13/624,332 Advisory Office Action dated Oct. 13, 2016.
U.S. Appl. No. 13/624,386 Office Action dated Nov. 28, 2016.
U.S. Appl. No. 14/014,168 Final Office Action dated Sep. 1, 2016.
Usami, et al. The effect of pH, hydrogen peroxide and temperature on the stability of human monoclonal antibody. J Pharm Biomed Anal. Jun. 1996;14(8-10):1133-40.
Volk, et al. The accuracy of primary care patients' self-reports of prostate-specific antigen testing. Am J Prev Med. Jan. 2002;22(1):56-8.
Wang, Y., et al. Detection of Mammary Tumor Virus ENV Gene-like Sequences in Human Breast Cancer. (Nov. 15, 1995) Cancer Research vol. 55, pp. 5173-5179.
Wilk et al., Integrated electrodes on a silicon based ion channel measurement platform, Biosensors and Bioelectronics, Sep. 2007, 183-190, vol. 23, No. 2.
Williams et al., Creating protein affinity reagents by combining peptide ligands on synthetic DNA scaffolds, J. Am Chem Soc., Dec. 2009, 17233-17241, vol. 131, No. 47.
Yang, et al. Segmentation and intensity estimation for microarray images with saturated pixels. BMC Bioinformatics. Nov. 30, 2011;12:462. doi: 10.1186/1471-2105-12-462.
Zhang et al., Reversible oxygen gas sensor based on electrochemiluminescence., Chemical Communications, May 2010, 3333-3335, vol. 46, No. 19.
Zhou, Z.H., et al. Properties and function of polyreactive antibodies and polyreactive antigen-binding B cells. (Dec. 2007) J. Autoimmun. vol. 29, No. 4, pp. 219-228.
Zundel, et al. Development and evaluation of an enzyme-linked immunoassay for the prostate: specific antigen utilizing two monoclonal antibodies. Urol Res. 1990;18(5):327-30.

* cited by examiner

FIGURE 1

CONDITIONED SURFACES FOR IN SITU MOLECULAR ARRAY SYNTHESIS

CROSS-REFERENCE

This application claims the benefit of U.S. Provisional Application No. 62/218,418, filed Sep. 14, 2015, which is incorporated herein by reference in its entirety.

GOVERNMENT SUPPORT

This invention was made with government support under 1243082 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Nov. 28, 2016, is named 42206-708_201_SL.txt and is 3,456 bytes in size.

BACKGROUND

Array technologies allow for large-scale, quantitative analyses of biological samples. However, the density and robustness of such technologies should be improved to allow increased sensitivity, reproducibility and accuracy of biological assays using such arrays.

SUMMARY OF THE INVENTION

Disclosed herein are methods and devices for making an array, the method comprising (a) performing a conditioning step on a surface of the array in the absence of monomer; (b) repeating step (a) at least once; (c) performing a synthesis step upon the surface to add at least one monomer; and (d) repeating step (c) at least once to form a sequence, wherein the conditioning step performed prior to synthesizing the sequence enhances attachment of the sequence to the surface of the array.

In some embodiments, the method comprises the conditioning step to be performed at least 5 times, at least 10 times or at least 15 times. In other embodiments, the binding of a target to a sequence is enhanced by the methods and devices disclosed herein by least 10%, at least 20%, at least 30%, at least 40% or at least 50%. In yet other embodiments, the binding of a target to a sequence is enhanced by the methods and devices disclosed herein by least 1-fold, at least 2-fold, at least 3-fold, at least 4-fold, at least 5-fold, at least 6-fold, at least 7-fold, at least 8-fold, at least 9-fold, at least 10-fold, or at least 15-fold. In still other embodiments, the sensitivity of the array is enhanced by the methods and devices disclosed herein by at least 10%, at least 20%, at least 30%, at least 40% or at least 50%. In still other embodiments, the sensitivity of the array is enhanced by the methods and devices disclosed herein by at least 1-fold, at least 2-fold, at least 3-fold, at least 4-fold, at least 5-fold, at least 6-fold, at least 7-fold, at least 8-fold, at least 9-fold, at least 10-fold, or at least 15-fold.

Also disclosed herein are methods and devices for making an array, comprising (a) performing a chemical reaction upon the array that is capable of attaching a monomer to a coupling site, wherein the monomer forms part of a linker sequence; (b) performing an additional chemical reaction upon the array that is capable of adding a monomer to the attached monomer of step (a); (c) repeating step (b) at least once until the monomers that comprise the desired linker sequence have been added; and d. synthesizing in situ a functional sequence onto the free end of the linker sequence, wherein the linker sequence enhances binding between the functional sequence and a substrate.

In some embodiments, the methods and devices disclosed herein to make an array include a linker sequence between 2 and 5 monomers, between 6 and 10 monomers, between 11 and 15 monomers, between 16 and 20 monomers, between 21 and 25 monomers, between 26 and 30 monomers, or at least 30 monomers. In yet other embodiments, the linker sequences is at least 10% homogeneous, at least 20% homogeneous, at least 30% homogeneous, at least 40% homogeneous, at least 50% homogeneous, at least 60% homogeneous, at least 70% homogeneous, at least 80% homogeneous, at least 90% homogeneous, or at least 100% homogeneous.

In still other embodiments, the linker sequence has a net negative charge at a pH of 7. In other embodiments, the linker sequence has a net positive charge at a pH of 7. In yet other embodiments, the linker sequence has a neutral charge at a pH of 7.

In other embodiments, the linker sequence is composed of molecules selected from the group consisting of nucleotides, oligonucleotides, polynucleotides, ribonucleotides, oligoribonucleotides, polyribonucleotides, monosaccharides, oligosaccharides, polysaccharides, amino acids, peptides, polypeptides, proteins, lipids, synthetic or non-natural compounds, and peptide nucleic acids (PNAs). In additional embodiments, the linker sequence is composed of amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, selenocysteine, pyrrolysine, N-formylmethionine, L-theanine, gamma amino butyric acid (GABA), ornithine, citrulline, α-methylnorvaline, β-alanine, δ-aminolevulinic acid, and 4-aminobenzoic acid (PABA). In other embodiments, the linker sequence is homogeneously composed of glycine. In yet other embodiments, the linker sequence comprises at least one monomer unit of polyethylene glycol (PEG), diamines, diacids, amino acids, alcohols, thiols, or combinations thereof.

Also disclosed herein are arrays comprising: a. a surface, and b. a plurality of molecules, wherein the molecules comprise a linker sequence comprised of monomers and having two ends, wherein one end is coupled to the surface and the other end is coupled to a functional sequence which binds a target molecule. Also disclosed herein are arrays comprising: (a) a surface, and (b) a plurality of in situ synthesized molecules immobilized to the surface, wherein each molecule comprises a linker attached to a functional sequence, the linker being at least 1 monomer in length and interposed between the surface of the array and the functional sequence, and the functional sequence being at least 2 monomers in length.

Disclosed herein are peptide arrays comprising: (a) a surface, and (b) a plurality of peptides immobilize to the surface, wherein each peptide comprises a linker sequence attached to a functional sequence, the linker sequence being interposed between the surface of the array and the functional sequence. Also disclosed herein are methods of making an array of molecules, comprising: a. performing a first chemical reaction on the array, wherein a pre-synthesized linker is attached to a surface of the array; and b. performing a second chemical reaction upon the array, wherein a pre-synthesized functional sequence is attached to the linker sequence, wherein the linker sequence enhances binding between the functional sequence and a target.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

Figure 1:
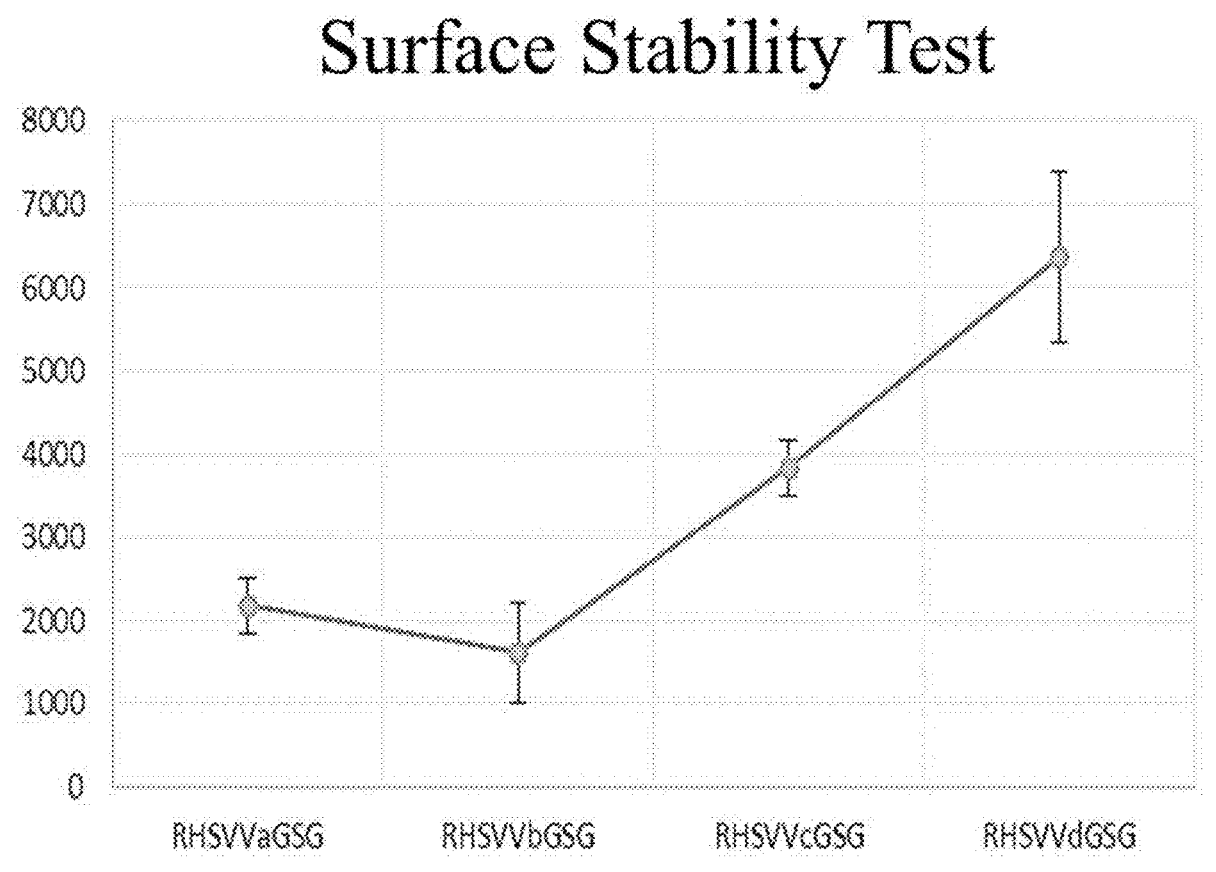

FIG. 1 illustrates the results of the surface stability test performed upon peptides synthesized successively. The y-axis is binding strength. Along the x-axis are the sequences of peptides synthesized. The lower case letters (a,b,c,d) represent the order in which the monoclonal antibody epitope RHSVV sequences (SEQ ID NO: 1) were synthesized. Thus, the sequence RHSVVa (SEQ ID NO: 1) was synthesized first and was subjected to all of the conditions associated with synthesizing RHSVVb (SEQ ID NO: 1), RHSVVc (SEQ ID NO: 1) and RHSVVd (SEQ ID NO: 1). As can be seen, sequences made later in the synthesis resulted in greater binding, presumably because there was less opportunity of removal or modification. The Ab1 epitopes were on aminosilane surface without stabilization cycles.

FIG. 2 is similar to FIG. 1 in terms of axis definitions. It illustrates the results of the surface stability test performed upon peptides synthesized successively on a seven amino acid linker (SEQ ID NO: 5). The Ab1 epitopes (all disclosed as SEQ ID NO: 8) were synthesized 4 times, labeled with a, b, c, d, on amino silane surface after 20 stabilization cycles; the linkers are synthesized during the stabilization cycles.

FIG. 3 is similar to FIG. 1 in terms of axis definitions. It illustrates the results of the surface stability test performed upon peptides synthesized successively on a three amino acid linker. The Ab1 epitopes (all disclosed as SEQ ID NO: 7) were synthesized 4 times, labeled with a, b, c, d, on aminosilane surface after 20 stabilization cycles; the linkers are synthesized during the stabilization cycles.

FIG. 4 illustrates the results of the surface stability test as a function of the length and composition of various linkers. The Ab1 epitopes were synthesized 4 times, labeled with a, b, c, d, on an aminosilane surface after 20 stabilization cycles; the linkers are synthesized during the stabilization cycles. Figure discloses SEQ ID NOS 7, 9-11, 8, 12, 7, 9-11, 8, 12, 7, 9-11, 8, 7, 9-11, 8, 12, 13, 2-6 and 14, respectively, in order of appearance.

FIG. 5 is a visual representation of an immunosignature as a heat map. The x axis represents specific peptide features on the array used. The y axis represents specific samples applied to the array. The samples were taken from individuals that had Dengue fever (Dengue), Malaria, West Nile Virus (WNV) or had no disease (ND). The top sample was a control in which the fluorescently labeled secondary antibody used to detect IgG binding in the other samples is used in the absence of a blood sample.

DETAILED DESCRIPTION OF THE INVENTION

Arrays can be generated using methods that include immobilizing purified molecules or monomers onto suitable surfaces or synthesizing them in situ directly on the surface. In situ synthesis offers significant advantages over other methods such as a greater number and density of features, and enhanced sensitivity, but the quality and reliability of in situ arrays can be contingent on the quality and consistency of the synthesized molecules. One important aspect of an in situ synthetic process is the preparation of the surface upon which in situ synthesis is performed. Factors that are important to in situ array synthesis can include the proper preparation of the surface, the availability of attachment groups that can be used as a base for attachment, the density of those groups, the tendency of the surface or matrix surrounding the attachment groups to interfere with the function of the final synthesized molecule, for example through nonspecific binding or by modifying the synthesized molecule to interact with a molecular partner of choice, and the evenness of the distribution of attachment groups of multiple length.

Different methods exist for placing attachment groups on surfaces. One of the most common surface modifications, particularly for surfaces that have a large fraction of silicon oxide, is to use a functionalized silane, for example an amino silane. Depending on the chemistry of attachment, such molecules can add to the surface in a well-defined layer or as a more complex cross-linked structure. In situ synthesis steps can then be performed upon the attachment groups on the surface by exposing them to monomers in reactive coupling steps that link them together.

The present disclosure recognizes the advantages of preparing conditioned surfaces for in situ molecular array synthesis. Some arrays, such as the arrays described in PCT/US2013/065541 and U.S. Pat. No. 5,424,186, hereinafter incorporated by reference in their entireties, provide a method of analyzing various materials including biological samples. However, the sensitivity and consistency of array-based detection can depend upon the properties of the attachment groups and the surface on which they reside.

Recognized herein is that molecules of previously described arrays are not all equally available for binding on the array. Such variability can lead to differences in sensitivity between features on or between arrays, and thus reproducibility of biological assay results on these arrays. The present disclosure recognizes that compensation can be made for this variability by increasing or growing a linker molecule or molecules on the attachment sites. Accordingly, included herein are methods to modify or increase the length of linkers on attachment sites of the arrays in order to optimize binding of targets in the biological samples to molecules attached to the array.

Also recognized herein is that the attachment groups of previously described arrays are not all equally available for reactive coupling. Moreover, the present disclosure recognizes that the surface material of an array is not entirely functionally inert (both in terms of the synthesis and the final function of the molecule) at locations other than the chemical attachment site. The present disclosure also recognizes that the structure of the silane or other attachment matrices can be affected by the synthetic process. As a consequence, some in situ synthesis methods may lead to the generation of surfaces with different properties in earlier synthetic steps versus later synthetic steps.

Figure 2:
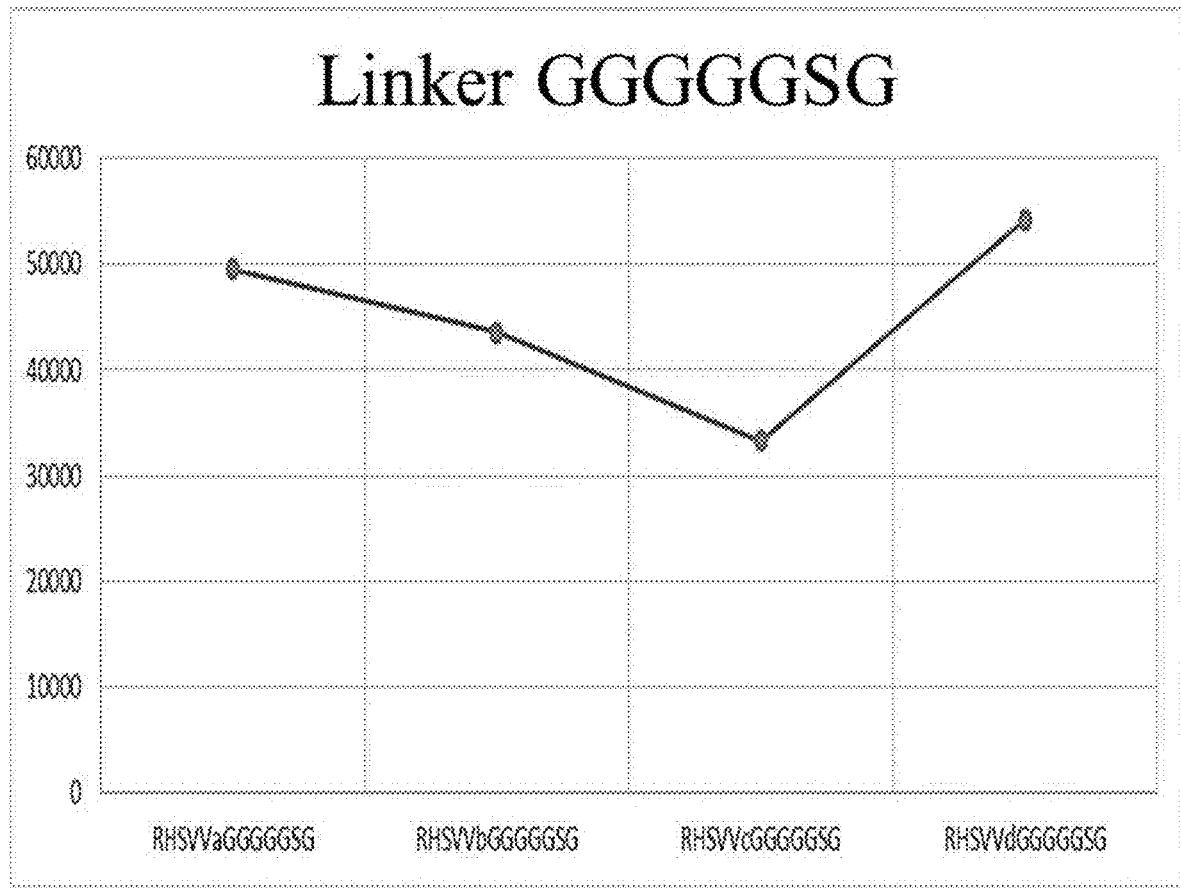
Figure 3:
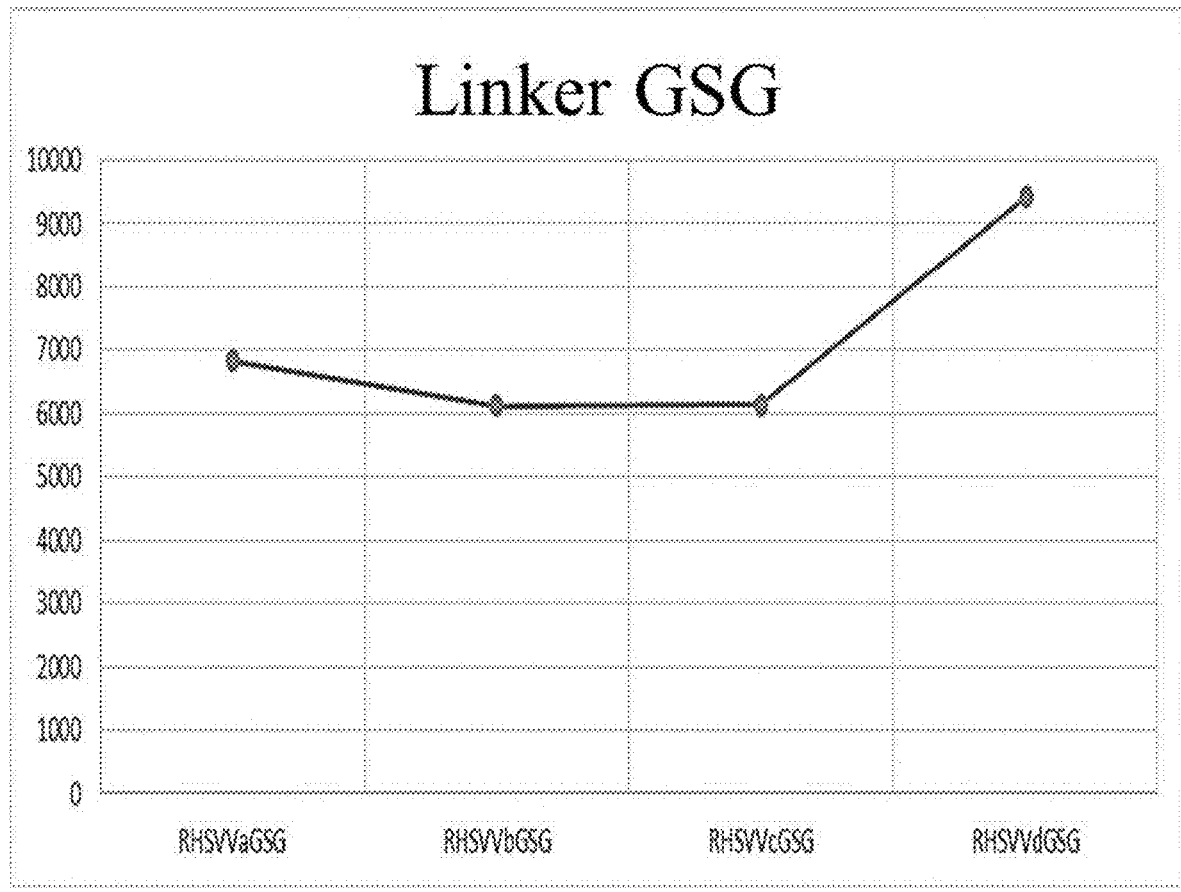
Figure 4:
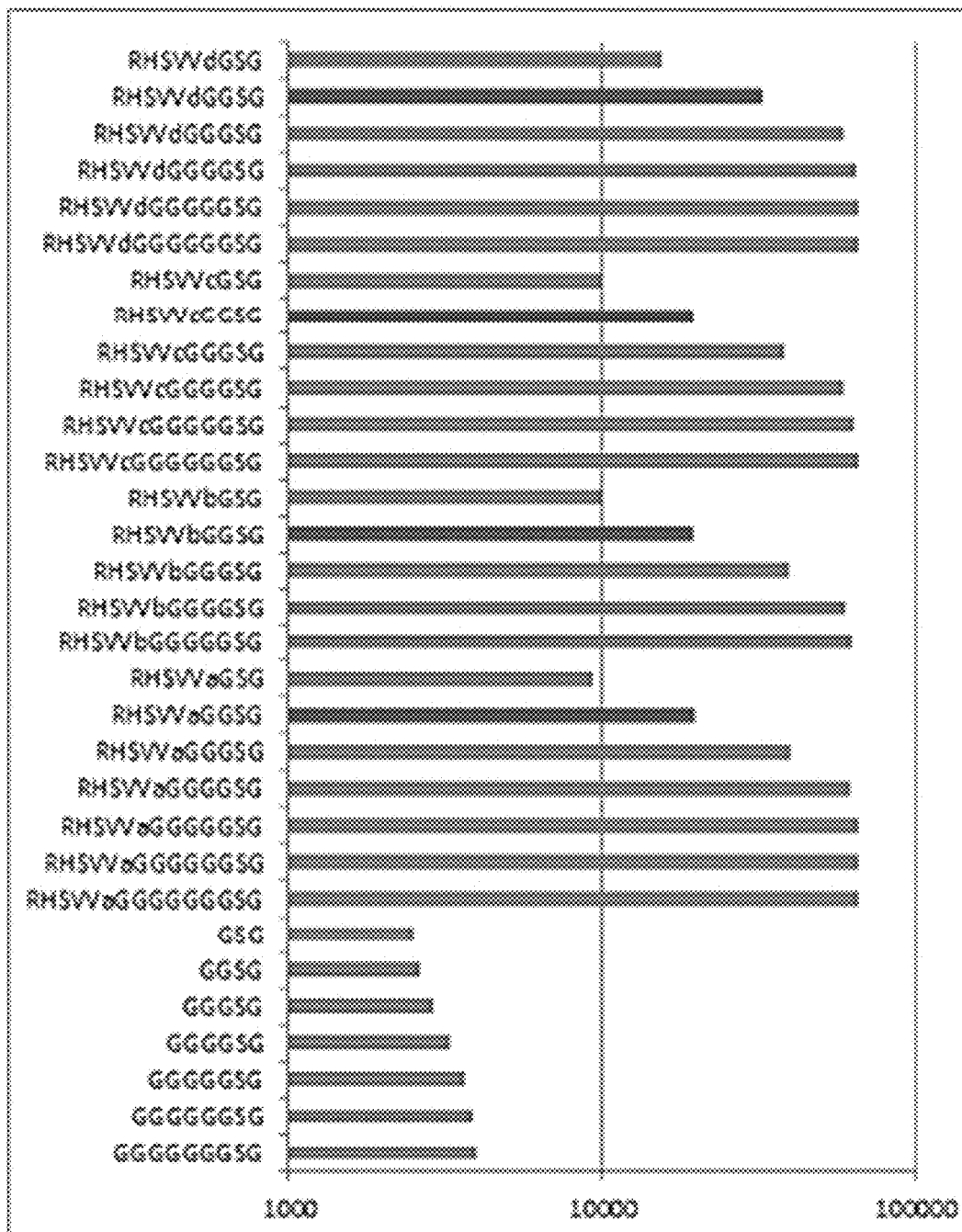

Described herein are methods for in situ synthesis of arrays that significantly enhances attachment of a sequence to the surface of the array. These methods allow for the production of arrays with enhanced sensitivity that are applicable to a wide variety of applications, including but not limited to: diagnostic arrays, arrays for selection of specific ligands or targets, arrays for potential drugs, and arrays of sensor molecules. In some cases, the approach can comprise performing multiple cycles (or partial cycles) of surface conditioning prior to the main synthesis, thereby allowing a surface to become stabilized before the molecules or sequences are actually in situ synthesized, or otherwise incorporated, into the array. The result can be an array wherein the molecules or sequences bind to their ligands or targets with greater sensitivity and reduced background noise.

In some cases, the cycles are run in such a way that no coupling of a new molecular component to the system can occur prior to the main synthesis. In other cases, the cycles are run in such a way that coupling of a new molecular component to the system can occur prior to the main synthesis. In yet other cases, the process involves a combination of cycles that couple new molecular components to the system and cycles that do not couple new molecular components to the system prior to the main synthesis. In some instances, the process involves growing a "linker" on the attachment sites that is attached to a molecule or sequence prior to the main synthesis.

Also provided herein is method of providing a conditioned surface to an array. In some cases, the surface comprises a number of in situ synthesized molecules attached to a conditioned surface. The surface can comprise a number of molecules that have been synthesized in situ or otherwise added to the array.

Definitions

Terms that are not defined in the present application or any incorporated references will be given their plain and ordinary meaning in the field as understood by one of ordinary skill in the art.

As used in the present specification, the following words, phrases and symbols are generally intended to have the meanings as set forth below, except to the extent that the context in which they are used indicates otherwise. The following abbreviations and terms have the indicated meanings throughout:

As used in the specification and claims, the singular forms "a", "an" and "the" include plural references unless the context clearly dictates otherwise. For example, the term "an array" may include a plurality of arrays unless the context clearly dictates otherwise.

An "array" refers to an intentionally created collection of molecules or sequences attached to or fabricated on a substrate or surface in which the identity or source of a group of molecules is known based on its location on the array. The molecules or sequences housed on the array and within a feature of an array can be identical to or different from each other.

Molecules can include nucleotides, oligonucleotides, polynucleotides, ribonucleotides, oligoribonucleotides, polyribonucleotides, monosaccharides, oligosaccharides, polysaccharides, amino acids, peptides, polypeptides, proteins, lipids, synthetic or non-natural compounds, peptide nucleic acids (PNAs) and other materials known in the art. In some embodiments, the molecules are a plurality of monomers that form a polymeric sequence. In other embodiments, the polymeric sequences bind to or recognize a target, e.g., ligand or binding partner, in a sample or specimen. In yet other embodiments, the molecules or polymeric sequences may include a linker as described herein.

Monomers can include nucleotides, monosaccharides, amino acids, and other subunit components. Monomer molecules can include natural amino acids, non-natural amino acids, nucleic acids, and analogues thereof.

A polymer can comprise two or more linked monomers. The monomers in a particular polymeric linker are not necessarily identical and can be of heterogeneous composition, comprising different monomers of the same class of molecules.

A class of molecules can be each of the following: nucleotides, oligonucleotides, polynucleotides, ribonucleotides, oligoribonucleotides, polyribonucleotides, monosaccharides, oligosaccharides, polysaccharides, amino acids, peptides, polypeptides, proteins, lipids, synthetic or non-natural compounds, or peptide nucleic acids (PNAs).

Polymers can be copolymers such as alternating copolymers, periodic copolymers, statistical copolymers, or block copolymers. Polymers can comprise linear or branched structures. Branched structures can result when one or more substituents or side groups on a parent polymeric chain are replaced by another chain of a polymer. The substituted polymeric chain or branch or side chain can be comprised of the same class or classes of monomers, or of different class or classes of monomers from the parent polymeric chain. In some branched structures, the side chains can grow off the parent chain at regular intervals such as every 10 monomeric subunits. In others, the side chains can grow off the parent chain at irregular intervals. A branched polymer can be a graft polymer, a star-shaped polymer, a comb polymer, or a dendrimer. Polymers can also form a polymer network in which all polymer chains are interconnected through branching and/or crosslinking to form a macroscopic entity. Crosslinking can occur between branches on the same polymer or between branches of distinct polymers. Where linear and branched polymers are in proximity, crosslinking can also occur between those linear and branched polymers. The three-dimensional structure of a polymer can be lacking a defined structure. For example, the polymer may be a flexible loop that lacks active sites capable of bonding or interacting with other sites on that same loop or with other molecules, which can cause its orientation and shape to continually change. Conversely, a polymer can form a more defined structure. For example, a peptide polymer may interact with itself or with neighboring polymers to form secondary, tertiary, and/or quaternary structures.

Main synthesis can comprise the synthesis steps that couples monomers to an attachment group on the surface or to other molecules already coupled to the attachment group. The added monomer can comprise a functional sequence or an inert sequence.

A "linker" can be either sequentially or non-sequentially incorporated into an array. A linker can be added to a growing polymer, or vice versa. A linker can be a component that elongates the distance between the substrate surface of an array and a molecule, such as a polypeptide or polynucleotide. A "linker sequence" can be a polymer of linker components. A "linker" can mean a linker component (including but not limited to a nucleotide, an amino acid or a chemical constituent), a linker sequence, and/or a linker polymer.

A "functional sequence" or "functional molecule" can recognize or bind to a target, e.g, ligand or binding partner to the functional sequence or functional molecule.

A "target" is a ligand or binding partner which can bind or interact with one or more functional molecules or sequences on the surface of an in situ synthesized array.

Couple or coupling comprises forming a chemical bond between two components, including but not limited to two molecules or sequences, or to a molecule or sequence and a linker, or to a molecule and an attachment site. The coupling moieties includes but is not limited to phosphodiester or amide bonds, ester bonds, thioester bonds, ether bonds, and carbon-carbon bonds.

Attach or attachment is equivalent to couple or coupling. An attachment site is a chemical or component that is capable of forming a chemical bond with another molecule. This includes but is not limited to phosphodiester or amide bonds, ester bonds, thioester bonds, ether bonds, and carbon-carbon bonds.

A surface can be a "solid support," "support," and "substrate," that serves as a physical support for a polymer or a group of polymers.

Linkers

A molecule can be attached to a surface directly or via a linker as disclosed herein. Direct attachment is possible by covalent attachment of a molecule, such as an amino acid to a region or feature of the surface. For example, the linker(s) as disclosed herein could be attached to a chemically reactive or chemically inert region of the surface. Optionally or additionally, the linkers may be linear or branched, having at least one or a multiplicity of reactive sites for attachment of a molecule as described herein. A linker can be cleavable, non-cleavable, self-immolating, hydrophilic, or hydrophobic. A linker as disclosed herein can also be flexible or rigid, or a combination thereof, which may be dependent upon the specific linker sequence employed. For example, glycine-rich linkers tend to be flexible, whereas proline-rich linkers tend to form relatively rigid extended structures.

A linker as disclosed herein can be a component that is sequentially or non-sequentially incorporated into an array. For example, a linker as disclosed herein may be formed on the surface of an array by sequentially attaching a linker component to an attachment site (e.g., aminosilane) followed by additional linker components that are added to the growing polymer. Alternatively, a linker polymer as disclosed herein may be prefabricated or pre-synthesized and then attached to the array surface without in situ sequential addition of linker molecules. Likewise, as disclosed herein a pre-synthesized molecule or sequence may be attached to an in situ synthesized linker or a pre-synthesized linker. In addition, as disclosed herein a combination of prefabricated linker polymers and in situ synthesis of additional linkers may be utilized to generate the finished linker polymer on the array surface.

In some embodiments, a linker as disclosed herein can be divided into separate linkers or sub-linkers by an intervening functional molecule or functional sequence. For example, a first linker or sub-linker may be attached to the attachment group on the array surface on one end, wherein an intervening functional sequence is joined or attached to the free end of the first linker, and a second linker may be then joined or attached to the free end of the intervening functional sequence. A second intervening functional sequence may then be joined to the free end of the second linker, and so on and so forth, wherein a polymer is generated that comprises a chain of alternating linker sequences and functional sequences.

A linker as disclosed herein can comprise a single monomer linked together, or it can comprise two or more linked monomers. Thus, the monomers in a particular polymeric linker are not necessarily identical and can be of heterogeneous composition, comprising different monomers of the same class. For example, valine and glycine are different monomers within the same class of amino acids. Alternatively, linkers may comprise monomers that belong to different classes. For example, a linker as disclosed herein may comprise amino acids from different classes (e.g., acidic and basic amino acids) or amino acids and nucleotides. Additionally, a linker as disclosed herein may also comprise modified amino acids, including but not limited to amino acids modified with polyethylene glycol, long-chain amine, long-chain alcohol or polyene derivative.

Linkers as disclosed herein can be copolymers such as alternating copolymers, periodic copolymers, statistical copolymers, or block copolymers. Linkers as disclosed herein can comprise linear or branched structures. Branched structures can result when one or more substituents or side groups on a parent polymeric chain are replaced by another chain of a polymer. The substituted polymeric chain or branch or side chain can be comprised of the same class or classes of monomers, or of different class or classes of monomers from the parent polymeric chain that forms part of the linker. In some branched structures, the side chains can grow off the parent chain at regular intervals such as every 10 monomeric subunits. In others, the side chains can grow off the parent chain at irregular intervals. A branched polymer linker as disclosed herein can be a graft polymer, a star-shaped polymer, a comb polymer, or a dendrimer. Linkers as disclosed herein can also form a polymer network in which all polymer chains are interconnected through branching and/or crosslinking to form a macroscopic entity. Crosslinking can occur between branches on the same linker or between branches of distinct linkers. Where linear and branched linkers are in proximity, crosslinking can also occur between those linear and branched linkers. The three-dimensional structure of a linker as disclosed herein can be lacking a defined structure. For example, the linker as disclosed herein may be a flexible loop that lacks active sites capable of bonding or interacting with other sites on that same loop or with other linker components, which can cause its orientation and shape to continually change. Conversely, a linker as disclosed herein can form a more defined structure. For example, a peptide linker as disclosed herein may interact with itself or with neighboring components to form secondary, tertiary, and/or quaternary structures.

The linkers as disclosed herein may be, for example, aryl acetylene, ethylene glycol oligomers containing 2-20 monomer units, 2-10 monomer units or 1-5 monomer units including but not limited to polyethylene glycol (PEG), diamines, diacids, amino acids, alcohols, thiols, and combinations thereof. Examples of diamines include ethylene diamine and diamino propane. Alternatively, the linkers as disclosed herein may be the same type as that being synthesized (i.e., nascent polymers), such as polypeptides and polymers of amino acid derivatives such as for example, amino hexanoic acids. While most natural amino acids are alpha amino acids, linkers can comprise monomeric subunits selected from alpha, beta, gamma, delta, and/or epsilon amino acids. Linkers as disclosed herein may comprise amino acid monomers in either the L or D isomeric forms. Linkers as disclosed herein can include monomeric subunits selected from the 20 standard proteinogenic amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments, the amino acids C, I, T and M, and optionally Q and E, are not included as subunits in the linker. Linkers as disclosed herein may also have monomeric subunits selected from non-standard proteinogenic amino acids such as selenocysteine, pyrrolysine, and N-formylmethionine. Linkers may also have monomeric subunits selected from non-proteinogenic amino acids, which can include L-theanine, gamma amino butyric acid (GABA), ornithine, citrulline, α-methylnorvaline, β-alanine, δ-Aminolevulinic acid, and/or 4-Aminobenzoic acid (PABA). Similarly, the linkers may comprise polymers as defined in this specification. For example, linkers as disclosed herein can comprise nucleic acids (DNA or RNA), oligosaccharides or polysaccharides, lipids, fatty acids, peptide nucleic acids, synthetic compounds, or analogues thereof.

Linkers as disclosed herein may be of homogeneous or heterogeneous composition. For example, in some embodiments a linker as disclosed herein may be a peptide linker homogeneously composed of only alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, selenocysteine, pyrrolysine, N-formylmethionine, L-theanine, gamma amino butyric acid (GABA), ornithine, citrulline, α-methylnorvaline, β-alanine, β-Aminolevulinic acid, or 4-Aminobenzoic acid (PABA) monomers. In other embodiments, a peptide linker as disclosed herein may be heterogeneously composed of more than one type of monomer selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, selenocysteine, pyrrolysine, N-formylmethionine, L-theanine, gamma amino butyric acid (GABA), ornithine, citrulline, α-methylnorvaline, β-alanine, δ-Aminolevulinic acid, and 4-Aminobenzoic acid (PABA) monomers. A heterogeneous linker as disclosed herein composition may be at least of a certain homogeneous percentage. For example, a linker composed of 50% Alanine, 10% Glycine, 10% Isoleucine, 10% Tryptophan, 10% Serine, and 10% Glutamine is 50% homogeneous. The highest percentage component is the homogeneous percentage.

In some embodiments, a linker as disclosed herein comprises a composition that is at least 10% homogeneous, 20% homogeneous, 30% homogeneous, 40% homogeneous, 50% homogeneous, 60% homogeneous, 70% homogeneous, 80% homogeneous, 90% homogeneous, or 100% homogeneous.

In some embodiments, a linker as disclosed herein comprises a composition that is no more than 10% homogeneous, 20% homogeneous, 30% homogeneous, 40% homogeneous, 50% homogeneous, 60% homogeneous, 70% homogeneous, 80% homogeneous, 90% homogeneous, or 100% homogeneous.

In some embodiments, a linker as disclosed herein comprises a composition that is 10% homogeneous, 20% homogeneous, 30% homogeneous, 40% homogeneous, 50% homogeneous, 60% homogeneous, 70% homogeneous, 80% homogeneous, 90% homogeneous, or 100% homogeneous.

The attachment(s) as disclosed herein between linkers or between a linker and an attachment site on an array surface can be via an amide bond, an ester bond, an ether bond, a carbamate bond, a carbon-nitrogen bond, a triazole, a macrocycle, an oxime bond, a hydrazone bond, immine bonds, a carbon-carbon single double or triple bond, a disulfide bond, thioester bond, or a thioether bond. Non-limiting examples of the functional groups for attachment include functional groups capable of forming, for example, an amide bond, an ester bond, an ether bond, a carbonate bond, a carbamate bond, or a thioether bond.

Non-limiting examples of functional groups capable of forming such bonds include amino groups; carboxylic acid groups, hydroxyl groups, carboxyl groups; aldehyde groups; azide groups; aniline groups, pyrrole groups, nitrile groups, isonitrile groups, aziridine groups, alkyne and alkene groups; ketones; hydrazides; acid halides such as acid fluorides, chlorides, bromides, and iodides; acid anhydrides, including symmetrical, mixed, and cyclic anhydrides; carbonates; carbonyl functionalities bonded to leaving groups such as cyano, succinimidyl, and N-hydroxysuccinimidyl; hydroxyl groups; sulfhydryl groups; and compounds and components possessing, for example, alkyl, alkenyl, alkynyl, allylic, or benzylic leaving groups, such as halides, mesylates, tosylates, triflates, epoxides, phosphate esters, sulfate esters, and besylates.

A linker as disclosed herein may have one or more functional groups, for example, one functional group that is bonded to the surface, and one functional group that is bonded to the growing chain (e.g.: peptide chain), and a linking portion between the two functional groups. Non-limiting examples of the linking portion include alkylene, alkenylene, alkynylene, polyenes, sugars, sugar polymers, nucleic acids, nucleic acid polymers, fatty acids, lipids, polyether, such as polyethylene glycol (PEG), polyester, polyamide, polyamino acids, polypeptides, cleavable peptides, valine-citrulline, substituted phenyl derivatives (for example, hydroxy benzoic acid), aminobenzylcarbamates, D-amino acids, and polyamine, any of which being unsubstituted or substituted with any number of substituents, such as halogens, hydroxyl groups, sulfhydryl groups, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, urethane groups, epoxides, and ester groups.

Examples of peptide linkers as disclosed herein include the following sequences: GSG, GGSG (SEQ ID NO: 2), GGGSG (SEQ ID NO: 3), GGGGSG (SEQ ID NO: 4), GGGGGSG (SEQ ID NO: 5), and GGGGGGSG (SEQ ID NO: 6) (see, e.g., experiments shown on FIGS. 2-5 herein). Other examples contemplate even longer sequences that result from the sequential coupling of additional glycine monomeric subunits or other amino acid subunits to the growing peptide linker.

In some embodiments, a linker as disclosed herein can maintain a net positive charge at a pH of about 0, a pH of about 1, a pH of about 2, a pH of about 3, a pH of about 4, a pH of about 5, a pH of about 6, a pH of about 7, a pH of about 8, a pH of about 9, a pH of about 10, a pH of about 11, a pH of about 12, a pH of about 13, or a pH of about 14.

In some embodiments, a linker as disclosed herein can maintain a net negative charge at a pH of about 0, a pH of about 1, a pH of about 2, a pH of about 3, a pH of about 4, a pH of about 5, a pH of about 6, a pH of about 7, a pH of about 8, a pH of about 9, a pH of about 10, a pH of about 11, a pH of about 12, a pH of about 13, or a pH of about 14.

In some embodiments, a linker as disclosed herein can maintain a net neutral charge at a pH of about 0, a pH of about 1, a pH of about 2, a pH of about 3, a pH of about 4, a pH of about 5, a pH of about 6, a pH of about 7, a pH of about 8, a pH of about 9, a pH of about 10, a pH of about 11, a pH of about 12, a pH of about 13, or a pH of about 14.

In some embodiments, a linker as disclosed herein can maintain a net positive charge at a pH above 0 and up to and including 1, a pH above 1 and up to and including 2, a pH above 2 and up to and including 3, a pH above 3 and up to and including 4, a pH above 4 and up to and including 5, a pH above 5 and up to and including 6, a pH above 6 and up to and including 7, a pH above 7 and up to and including 8, a pH above 8 and up to and including 9, a pH above 9 and up to and including 10, a pH above 10 and up to and including 11, a pH above 11 and up to and including 12, a pH above 12 and up to and including 13, or a pH above 13 and up to and including 14. In some embodiments, a linker can maintain a net negative charge at a pH above 0 and up to and including 1, a pH above 1 and up to and including 2, a pH above 2 and up to and including 3, a pH above 3 and up to and including 4, a pH above 4 and up to and including 5, a pH above 5 and up to and including 6, a pH above 6 and up to and including 7, a pH above 7 and up to and including 8, a pH above 8 and up to and including 9, a pH above 9 and up to and including 10, a pH above 10 and up to and including 11, a pH above 11 and up to and including 12, a pH above 12 and up to and including 13, or a pH above 13 and up to and including 14.

In some embodiments, a linker as disclosed herein can maintain a net neutral charge at a pH above 0 and up to and including 1, a pH above 1 and up to and including 2, a pH above 2 and up to and including 3, a pH above 3 and up to and including 4, a pH above 4 and up to and including 5, a pH above 5 and up to and including 6, a pH above 6 and up to and including 7, a pH above 7 and up to and including 8, a pH above 8 and up to and including 9, a pH above 9 and up to and including 10, a pH above 10 and up to and including 11, a pH above 11 and up to and including 12, a pH above 12 and up to and including 13, or a pH above 13 and up to and including 14.

In some embodiments, a linker as disclosed herein can reduce the background signal on an array by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, a linker as disclosed herein can increase the sensitivity of the array by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In some embodiments, a linker as disclosed herein increases the sensitivity of the array by at least 1-fold, at least 2-fold, at least 3-fold, at least 4-fold, at least 5-fold, at least 6-fold, at least 7-fold, at least 8-fold, at least 9-fold, at least 10-fold, or at least 15-fold.

In some embodiments, a linker as disclosed herein increases the specificity of the array, as compared to an array with a decreased length or shorter linker, by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In some embodiments, a linker as disclosed herein increases the specificity of the array, as compared to an array with a decreased length or shorter linker, by at least 1-fold, at least 2-fold, at least 3-fold, at least 4-fold, at least 5-fold, at least 6-fold, at least 7-fold, at least 8-fold, at least 9-fold, at least 10-fold, or at least 15-fold.

In some embodiments, a linker as disclosed herein increases the reproducibility of the array, as compared to an array with a decreased length or shorter linker, by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In some embodiments, a linker as disclosed herein increases the reproducibility of the array by at least 1-fold, at least 2-fold, at least 3-fold, at least 4-fold, at least 5-fold, at least 6-fold, at least 7-fold, at least 8-fold, at least 9-fold, at least 10-fold, or at least 15-fold.

In some embodiments, the linker as disclosed herein increases the signal to background ratio of an array by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In some embodiments, the linker as disclosed herein increases the signal to background ratio of an array by at least 1-fold, at least 2-fold, at least 3-fold, at least 4-fold, at least 5-fold, at least 6-fold, at least 7-fold, at least 8-fold, at least 9-fold, at least 10-fold, or at least 15-fold.

In some embodiments, a linker as disclosed herein has a length of 2 monomers, 3 monomers, 4 monomers, 5 monomers, 6 monomers, 7 monomers, 8 monomers, 9 monomers, 10 monomers, 11 monomers, 12 monomers, 13 monomers, 14 monomers, 15 monomers, 16 monomers, 17 monomers, 18 monomers, 19 monomers, 20 monomers, 21 monomers, 22 monomers, 23 monomers, 24 monomers, 25 monomers, 26 monomers, 27 monomers, 28 monomers, 29 monomers, 30 monomers, 31 monomers, 32 monomers, 33 monomers, 34 monomers, 35 monomers, 36 monomers, 37 monomers, 38 monomers, 39 monomers, 40 monomers, 41 monomers 42 monomers, 43 monomers, 44 monomers, 45 monomers, 46 monomers, 47 monomers, 48 monomers, 49 monomers, or 50 monomers.

In some embodiments, a linker as disclosed herein has a length between 2 and 5 monomers, between 6 and 10 monomers, between 11 and 15 monomers, between 16 and 20 monomers, between 21 and 25 monomers, between 26 and 30 monomers, between 31 and 35 monomers, between 36 and 40 monomers, between 41 and 45 monomers, between 46 and 50 monomers, between 51 and 55 monomers, between 56 and 60 monomers, between 61 and 65 monomers, between 66 and 70 monomers, between 71 and 75 monomers, between 76 and 80 monomers, between 81 and 85 monomers, between 86 and 90 monomers, between 91 and 95 monomers, or between 95 and 100 monomers.

In some embodiments, a linker as disclosed herein has a length of at least 2 monomers, 3 monomers, 4 monomers, 5 monomers, 6 monomers, 7 monomers, 8 monomers, 9 monomers, 10 monomers, 11 monomers, 12 monomers, 13 monomers, 14 monomers, 15 monomers, 16 monomers, 17 monomers, 18 monomers, 19 monomers, 20 monomers, 21 monomers, 22 monomers, 23 monomers, 24 monomers, 25 monomers, 26 monomers, 27 monomers, 28 monomers, 29 monomers, 30 monomers, 31 monomers, 32 monomers, 33 monomers, 34 monomers, 35 monomers, 36 monomers, 37 monomers, 38 monomers, 39 monomers, 40 monomers, 41 monomers 42 monomers, 43 monomers, 44 monomers, 45 monomers, 46 monomers, 47 monomers, 48 monomers, 49 monomers, or 50 monomers.

In some embodiments, a particular linker sequence as disclosed herein is between 1 and 3 monomers in length, or between 4 and 6 monomers in length, or between 7 and 9 monomers in length, or between 10 and 12 monomers in length, or between 13 and 15 monomers in length, or between 16 and 18 monomers in length, or between 19 and 21 monomers in length, or between 22 and 24 monomers in length, or between 25 and 27 monomers in length, or between 28 and 30 monomers in length, or between 31 and 33 monomers in length, or between 34 and 36 monomers in length, or between 37 and 39 monomers in length, or between 40 and 42 monomers in length, or between 43 and 45 monomers in length, or between 46 and 48 monomers in length, or between 49 and 51 monomers in length, or between 52 and 54 monomers in length, or between 55 and 57 monomers in length, or between 58 and 60 monomers in length, or between 61 and 63 monomers in length, or between 64 and 66 monomers in length, or between 67 and 69 monomers in length, or between 70 and 72 monomers in length, or between 73 and 75 monomers in length, or between 76 and 78 monomers in length, or between 79 and 81 monomers in length, or between 82 and 84 monomers in length, or between 85 and 87 monomers in length, or between 88 and 90 monomers in length, or between 91 and 93 monomers in length, or between 94 and 96 monomers in length, or between 97 and 99 monomers in length, or between 100 and 102 monomers in length.

In some embodiments, a particular functional sequence as disclosed herein has a length of 1 monomer, 2 monomers, 3 monomers, 4 monomers, 5 monomers, 6 monomers, 7 monomers, 8 monomers, 9 monomers, 10 monomers, 11 monomers, 12 monomers, 13 monomers, 14 monomers, 15 monomers, 16 monomers, 17 monomers, 18 monomers, 19 monomers, or 20 monomers.

In some embodiments, a particular functional sequence as disclosed herein has a length of at least 1 monomer, 2 monomers, 3 monomers, 4 monomers, 5 monomers, 6 monomers, 7 monomers, 8 monomers, 9 monomers, 10 monomers, 11 monomers, 12 monomers, 13 monomers, 14 monomers, 15 monomers, 16 monomers, 17 monomers, 18 monomers, 19 monomers, or 20 monomers.

In some embodiments, a particular functional sequence as disclosed herein is between 1 and 3 monomers in length, or between 4 and 6 monomers in length, or between 7 and 9 monomers in length, or between 10 and 12 monomers in length, or between 13 and 15 monomers in length, or between 16 and 18 monomers in length, or between 19 and 21 monomers in length, or between 22 and 24 monomers in length, or between 25 and 27 monomers in length, or between 28 and 30 monomers in length, or between 31 and 33 monomers in length, or between 34 and 36 monomers in length, or between 37 and 39 monomers in length, or between 40 and 42 monomers in length, or between 43 and 45 monomers in length, or between 46 and 48 monomers in length.

In some embodiments, a combined linker and sequence as disclosed herein has a length of at least 4 monomers, 5 monomers, 6 monomers, 7 monomers, 8 monomers, 9 monomers, 10 monomers, 11 monomers, 12 monomers, 13 monomers, 14 monomers, 15 monomers, 16 monomers, 17 monomers, 18 monomers, 19 monomers, or 20 monomers.

In some embodiments, a combined linker and functional sequence as disclosed herein is between 1 and 3 monomers in length, or between 4 and 6 monomers in length, or between 7 and 9 monomers in length, or between 10 and 12 monomers in length, or between 13 and 15 monomers in length, or between 16 and 18 monomers in length, or between 19 and 21 monomers in length, or between 22 and 24 monomers in length, or between 25 and 27 monomers in length, or between 28 and 30 monomers in length, or between 31 and 33 monomers in length, or between 34 and 36 monomers in length, or between 37 and 39 monomers in length, or between 40 and 42 monomers in length, or between 43 and 45 monomers in length, or between 46 and 48 monomers in length.

In some embodiments, the linker sequences as disclosed herein present on a surface are of a uniform length. For example, in certain embodiments, photolithography masks may not be utilized, wherein linker synthesis is conducted upon the entire array surface to produce linkers of uniform length. In other embodiments, the linker sequences present on a surface as disclosed herein are not of uniform length. For example, non-uniform linker sequences on a surface may arise from the use of photolithography masks during synthesis that result in differential addition of monomeric subunits to distinct features on the array surface. In certain embodiments, the linkers within a given feature can be of uniform length, while having a distinct length from linkers in a different feature.

In some embodiments, the linker sequences as disclosed herein will be of one uniform length for a subset of features and of a different uniform length for at least one other subset of features on the given surface.

Surfaces

A surface as disclosed herein can refer to a material or group of materials having rigid or semi-rigid properties. A surface can comprise one or more materials having porous, permeable, or semi-permeable properties. A surface can also comprise one or more materials having malleable, ductile, brittle, plastic or elastic properties. A surface can also comprise one or more materials having polar, charged, acidic, or basic properties.

A surface as disclosed herein can be a flat surface, or a round or curved surface (such as a bead). In certain embodiments of a flat surface, the shape of that surface may be a circle, an oval, an ellipse, a crescent, a triangle, a curvlinear triangle, a quatrefoil, a parallelogram, a square, a rhombus, a trapezoid, a kite, a pentagon, a hexagon, a heptagon, an octagon, a nonagon, or a decagon. In certain embodiments of a round or curved surface, the surface may take on the shape of a sphere, an ellipsoid, or a more complex shape. In some embodiments, at least one surface of the solid support can be substantially flat.

A surface as disclosed herein can be homogenous or heterogeneous. A surface can comprise physical elements such as wells, raised regions, bumps, indentations, towers, pins, etched trenches, or combinations thereof. In certain embodiments, the physical elements on the surface can be of roughly uniform dimensions. In certain embodiments, the physical elements on the surface can be of non-uniform dimensions. In certain embodiments, the physical elements occur on the surface at discrete locations in a non-repetitive pattern. In certain embodiments, the physical elements occur on the surface in a repetitive pattern. In such embodiments, repetitive physical elements that are adjacent to one another can be separated by a uniform distance. Alternatively, the repetitive physical elements that are adjacent to one another can be separated by non-uniform distances.

In some embodiments, the solid support may be porous.

Non-limiting examples of substrate or surface materials as disclosed herein include, for example, silicon, biocompatible polymers such as, for example poly(methyl methacrylate) (PMMA) and polydimethylsiloxane (PDMS), glass, SiO, (such as, for example, a thermal oxide silicon wafer such as that used by the semiconductor industry), quartz, silicon nitride, functionalized glass, gold, platinum, metalloporphyrins, tungsten, silica, diamond, titanium, polyester, polyamide, polyimide, polyether, polysulfone, fluoropolymer, and aluminum.

In certain embodiments, as disclosed herein an organosilane is used to provide the surface attachment group. In certain embodiments, the organosilane comprises aminosilane, epoxysilane, or fluorosilane.

Non-limiting examples of functionalized surfaces as disclosed herein include: amino-functionalized glass, carboxy functionalized glass, hydroxy functionalized glass, aldehyde functionalized glass, Streptavidin functionalized glass, Neutravidin functionalized glass, Avidin functionalized glass, Poly-L-Lysine functionalized glass, pyridine functionalized glass, and 3-aminopropyl-triethoxysilane (APTS) functionalized glass.

Additionally, a surface may optionally be coated with one or more layers to provide a surface for molecular attachment or functionalization, increased or decreased reactivity, binding detection, or other specialized application. In such embodiments, as disclosed herein the surface may be optionally coated with at least 1 layer, at least 2 layers, at least 3 layers, at least 4 layers, at least 5 layers, at least 6 layers, at least 7 layers, at least 8 layers, at least 9 layers, at least 10 layers, at least 11 layers, at least 12 layers, at least 13 layers, at least 14 layers, at least 15 layers, at least 16 layers, at least 17 layers, at least 18 layers, at least 19 layers, or at least 20 layers. In certain embodiments, the layers coated on the surface can provide cumulative properties such as increased molecular attachment or functionalization, increased or decreased reactivity, binding detection, or other specialized application. In certain embodiments, the layers coated on the surface can provide discrete properties such as one layer providing molecular attachment for one category of monomers or polymers while another layer provides molecular attachment for a different category of monomers or polymers. For example, one layer may provide molecular attachment for peptides, while a second layer provides molecular attachment for nucleic acids to form a combination array.

Substrate or surface materials and or layer(s) may be porous or non-porous. For example, a substrate may be comprised of porous silicon. Furthermore, the substrate or surface materials may be permeable or semipermeable. Additionally, the substrate as disclosed herein may be a silicon wafer or chip such as those used in the semiconductor device fabrication industry. In the case of a wafer or chip, a plurality of arrays may be synthesized on the wafer. In some embodiments, the substrate is chosen from glass, silicon and silicon having a silicon oxide layer.

Methods of Synthesis

In some embodiments as disclosed herein, a method for in situ synthesis of the array is photolithography-based. In some embodiments, the photolithography-based synthesis comprises a photomask patterned step.

In some embodiments as disclosed herein, a method for the photolithography-based synthesis of the arrays uses a minimum number of photomasks to construct the array. In some embodiments, the array comprises features of about 0.5 micron to about 200 microns in diameter and a center-to-center distance of about 1 micron to about 300 microns on center.

In some embodiments as disclosed herein, a feature is about 0.5 micron to about 10 microns in diameter; about 11 microns to about 20 microns in diameter; about 21 microns to about 30 microns in diameter; about 31 microns to about 40 microns in diameter; about 41 microns to about 50 microns in diameter; about 51 microns to about 60 microns in diameter; about 61 microns to about 70 microns in diameter; about 71 microns to about 80 microns in diameter; about 81 microns to about 90 microns in diameter; about 91 microns to about 100 microns in diameter; about 101 microns to about 110 microns in diameter; about 111 microns to about 120 microns in diameter; about 121 microns to about 130 microns in diameter; about 131 microns to about 140 microns in diameter; about 141 microns to about 150 microns in diameter; about 151 microns to about 160 microns in diameter; about 161 microns to about 170 microns in diameter; about 171 microns to about 180 microns in diameter; about 181 microns to about 190 microns in diameter; about 191 microns to about 200 microns in diameter.

In some embodiments as disclosed herein, the center-to-center distance between adjacent features is about 1 micron to about 10 microns; about 11 microns to about 20 microns; about 21 microns to about 30 microns; about 31 microns to about 40 microns; about 41 microns to about 50 microns; about 51 microns to about 60 microns; about 61 microns to about 70 microns; about 71 microns to about 80 microns; about 81 microns to about 90 microns; about 91 microns to about 100 microns; about 101 microns to about 110 microns; about 111 microns to about 120 microns; about 121 microns to about 130 microns; about 131 microns to about 140 microns; about 141 microns to about 150 microns; about 151 microns to about 160 microns; about 161 microns to about 170 microns; about 171 microns to about 180 microns; about 181 microns to about 190 microns; about 191 microns to about 200 microns; about 201 microns to about 210 microns; about 211 microns to about 220 microns; about 221 microns to about 230 microns; about 231 microns to about 240 microns; about 241 microns to about 250 microns; about 251 microns to about 260 microns; about 261 microns to about 270 microns; about 271 microns about 280 microns; about 281 microns to about 290 microns; about 291 microns to about 300 microns.

In some embodiments as disclosed herein, the array comprises at least 10,000 features, at least 20,000 features, at least 30,000 features, at least 40,000 features, at least 50,000 features, at least 60,000 features, at least 70,000 features, at least 80,000 features, at least 90,000 features, at least 100,000 features, at least 110,000 features, at least 120,000 features, at least 130,000 features, at least 140,000 features, at least 150,000 features, at least 160,000 features, at least 170,000 features, at least 180,000 features, at least 190,000 features, at least 200,000 features, at least 210,000 features, at least 220,000 features, at least 230,000 features, at least 240,000 features, at least 250,000 features, at least 260,000 features, at least 270,000 features, at least 280,000 features, at least 290,000 features, at least 300,000 features, at least 310,000 features, at least 320,000 features, at least 330,000 features, at least 340,000 features, at least 350,000 features, at least 360,000 features, at least 370,000 features, at least 380,000 features, at least 390,000 features, at least 400,000 features, at least 410,000 features, at least 420,000 features, at least 430,000 features, at least 440,000 features, at least 450,000 features, at least 460,000 features, at least 470,000 features, at least 480,000 features, at least 490,000 features, at least 500,000 features, at least 600,000 features, at least 700,000 features, at least 800,000 features, at least 900,000 features, or at least 1,000,000 features.

In some embodiments as disclosed herein, the surface of the array is conditioned or pre-conditioned prior to attachment of the sequences onto the surface of the array. Conditioning of the array surface includes exposing the features on the surface to the coupling and photoresist solutions in the absence of monomers to form sequences.

In some embodiments as disclosed herein, at least one pre-conditioning or conditioning step is performed on the surface prior to the main synthesis of the functional sequence.

In some embodiments as disclosed herein, the conditioning step is performed at least 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, or 30 times.

In some embodiments as disclosed herein, the conditioning step is performed no more than 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, or 30 times.

In some embodiments as disclosed herein, the conditioning step is performed 1 time, 2 times, 3 times, 4 times, 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, 24 times, 25 times, 26 times, 27 times, 28 times, 29 times, or 30 times.

In some embodiments, conditioning the surface of the array as disclosed herein can increase the sensitivity of the array by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In some embodiments, conditioning the surface of the array as disclosed herein can increase the sensitivity of the array by at least 1-fold, at least 2-fold, at least 3-fold, at least 4-fold, at least 5-fold, at least 6-fold, at least 7-fold, at least 8-fold, at least 9-fold, at least 10-fold, or at least 15-fold.

In some embodiments, conditioning the surface of the array as disclosed herein can increase the specificity of the array, as compared to an array with a decreased length or shorter linker, by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In some embodiments, conditioning the surface of the array as disclosed herein can increase the specificity of the array, as compared to an array in the absence of conditioning, at least 1-fold, at least 2-fold, at least 3-fold, at least 4-fold, at least 5-fold, at least 6-fold, at least 7-fold, at least 8-fold, at least 9-fold, at least 10-fold, or at least 15-fold.

In some embodiments, conditioning the surface of the array as disclosed herein can increase the reproducibility of the array, as compared to an array in the absence of conditioning, by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In some embodiments, conditioning the surface of the array as disclosed herein can increase the reproducibility of the array by at least 1-fold, at least 2-fold, at least 3-fold, at least 4-fold, at least 5-fold, at least 6-fold, at least 7-fold, at least 8-fold, at least 9-fold, at least 10-fold, or at least 15-fold.

In yet other embodiments, conditioning the surface of the array as disclosed herein can enhance binding of a target to the sequence on the array by at least 1%, at least 2%, at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

In still other embodiments, conditioning the surface of the array as disclosed herein can enhance binding of a target to the sequence on the array by at least 1-fold, at least 2-fold, at least 3-fold, at least 4-fold, at least 5-fold, at least 6-fold, at least 7-fold, at least 8-fold, at least 9-fold, at least 10-fold, or at least 15-fold.

EXAMPLES

Example 1: Multiple Successive Additions of a Specific Epitope

Steps (1) through (4) describe the generation of an array with multiple successive additions of a specific epitope:

Step (1). An 8 inch silicon wafer with a 2500 angstrom thermal oxide layer was cleaned extensively with a solution of sulfuric acid (83.5% in volume) and 30% hydrogen peroxide (16.5% in volume). This surface was extensively flushed with highly purified water. The wafer was then placed in a 0.5% solution by volume of aminopropyltriethoxysilane in 95% ethanol and 4.5% water and allowed to sit without agitation for 90 minutes. The wafer was next washed in ethanol and isopropanol, spin-dried and placed in an oven at 110° C. for 90 minutes. The wafer was then stored under nitrogen for two days. Then the wafer was placed on a spin coater and a 10 mL coupling solution of Boc-Gly (0.1M), 6-Cl-HOBT (0.1M) and diisopropylcarbodiimide (DIC, 0.1M) in N-methylpyrrolidinone (NMP) was added while spinning at 500 RPM. The wafer was then removed from the spin coater and a second clean wafer was placed on top of it in such a way that the coupling solution spun onto it was trapped between the two wafers. This arrangement was placed on a hot plate at 85° C. for 120 seconds. The cover plate was removed, the wafer was placed back on the spin coater and 10 mL of NMP was added as the wafer was spun at 2000 RPM to wash off the coupling solution. This coupling was repeated one more time before it was washed on a spin coater with solvents in order of 10 mL N-methylpyrrolidinone (NMP), 10 mL methylisobutylketone (MIBK), and 10 mL isopropanol (IPA) at 2000 RPM.

Step (2). The wafer was then placed on a spin coater and 10 mL of a photoresist solution (25 mg/ml poly methyl methacrylate (PMMA), 30 mg/ml Bis(4-t-butylphenyl)iodonium triflate (PAG), and 15 mg/mL isopropyl-9H-thioxanthen-9-one (ITX) in propylene glycol methyl ether acetate (PGMEA)) were added while spinning at 2000 RPM. The wafer was then kept at 75° C. for 1.5 minutes. The wafer was placed on an aligner and aligned to a precise position relative to a mask (within approximately 1-2 microns in the two horizontal dimensions and 10 microns in the vertical dimension). The mask was designed to expose certain features on the wafer to UV light centered at 365 nm. The wafer was exposed through the mask for 7 seconds using a total exposure power of 19 milliwatts/cm$^2$. The wafer was again placed on the spin coater, and 10 mL of methylisobutylketone (MIBK) was added while spinning at 2000 RPM to remove the photoresist. This was followed by 10 mL of isopropanol at the same speed. 10 mL of a coupling solution consisting of Boc-Ser (0.1M), DIC (0.1M), and 6-Cl-HOBT (0.1M) in NMP was then added while spinning at 500 RPM. The wafer was then removed from the spin coater and a second clean wafer was placed on top of it in such a way that the coupling solution spun onto it was trapped between the two wafers. This arrangement was placed on a hot plate at 85° C. for 120 seconds. The cover plate was removed, the wafer placed back on the spin coater and 10 mL of NMP was added as the wafer was spun at 2000 RPM to wash off the coupling solution. 10 mL of MIBK was then added as the wafer was spun at 2000 RPM, followed by 10 mL IPA at the same speed.

Step (3). The process described above in (2) was repeated 21 times, each time using an appropriate mask and amino acid. The amino acids were added in the following order: first=V; second=V; third=S; fourth=H; fifth=R; sixth=V; seventh=V; eight=S; ninth=H; tenth=R; eleventh=V; twelfth=V; thirteenth=S; fourteenth=H; fifteenth=R; sixteenth=V; seventeenth=V; eighteenth=S; nineteenth=H; twentieth=R; and each amino acid was added in same concentration of 0.1M as shown in (2). The one letter designation of each amino acid is used in the foregoing and that designation is well known to those skilled in the art.

Step (4). The wafer described above was diced in such a way that the arrays of ~330,000 peptides could be individually exposed to specific samples. In this way arrays were incubated with 5 pM of a monoclonal antibody P53Ab1. There were some peptides with the sequence RHSVVGSG (SEQ ID NO: 7) on the array. In some cases the RHSVV (SEQ ID NO: 1) part of the peptide was synthesized early in the synthesis (designated RHSVVaGSG (SEQ ID NO: 7) in FIG. 1), some successively later during the synthesis (designated RHSVVbGSG (SEQ ID NO: 7), RHSVVcGSG (SEQ ID NO: 7), and RHSVVdGSG (SEQ ID NO: 7)).

Example 2: Multiple Successive Additions of a Specific Epitope

The binding of the P53Ab1 monoclonal antibody to an array comprising each of the peptides described in EXAMPLE 1 was determined and is shown in FIG. 1. FIG. 1 illustrates the results of the surface stability test performed upon peptides synthesized successively. Each of the sequences on the x-axis was generated at successively later times during the synthesis. The y-axis shows the intensity of binding of the P53Ab1 monoclonal antibody to RHSVV sequences (SEQ ID NO: 1) that were synthesized early in the synthesis (labeled RHSVVaGSG (SEQ ID NO: 7) in FIG. 1), and to sequences that were synthesized later during the synthesis (labeled RHSVVbGSG (SEQ ID NO: 7), RHSV-VcGSG (SEQ ID NO: 7), and RHSVVdGSG (SEQ ID NO: 7) in FIG. 1). The data suggests that the later the functional sequence is synthesized in the process, the greater the intensity of binding to a target. This suggests that even though a feature is not having an amino acid added to it, the process of exposing the features on the surface to the coupling and the photoresist solutions increases the amount of peptide made that binds P53Ab1. In other words, the early synthetic cycles in the absence of an amino acid monomer precondition the feature for enhanced in situ synthesis. FIG. 1 illustrates an approximately 3-fold enhancement of binding when comparing the RHSVVaGSG (SEQ ID NO: 7) and RHSVVdGSG (SEQ ID NO: 7) peptides. This is surprising particularly because no additional monomers were added to the array between the pre-conditioning steps.

Example 3: Varying the Linker Length and Composition Before Successive Addition of a Specific Epitope Step (1). An 8 inch silicon wafer with a 2,500 angstrom thermal oxide layer was cleaned extensively with a solution of sulfuric acid (83.5% in volume) and 30% hydrogen peroxide (16.5% in volume). This surface was extensively flushed with highly purified water. The wafer was then placed in a 0.5% solution by volume of aminopropyltriethoxysilane in 95% ethanol and 4.5% water and allowed to sit without agitation for 90 minutes. The wafer was next washed in ethanol and isopropanol and then placed in an oven at 110° C. for 90 minutes. The wafer was then stored under nitrogen for two days. Then the wafer was placed on a spin coater, and a 10 mL coupling solution of Boc-Gly (0.1M), 6-Cl-HOBT (0.1M), and diisopropylcarbodiimide (DIC) in N-methylpyrrolidinone (NMP) was added while spinning at 500 RPM. The wafer was then removed from the spin coater and a second clean wafer was placed on top of it in such a way that the coupling solution spun onto was trapped between the two wafers. This arrangement was placed on a hot plate at 85° C. for 120 seconds. The cover plate was removed, the wafer placed back on the spin coater and 10 ml of NMP was added as the wafer was spun at 2000 RPM to wash off the coupling solution. The coupling was repeated one more time before it was washed on a spin coater in order of 10 mL NMP, 10 mL MIBK, and 10 mL IPA, each at 2000 RPM.

Step (2) The wafer was then placed on a spin coater and 10 mL of a photoresist solution (25 mg/ml poly methyl methacrylate (PMMA), 30 mg/ml Bis(4-t-butylphenyl)iodonium triflate (PAG) and 15 mg/mL isopropyl-9H-thioxanthen-9-one (ITX) in propylene glycol methyl ether acetate (PGMEA)) were added while spinning at 2,000 RPM. The wafer was then placed on a hot place at 75° C. for 1.5 minutes. The wafer was placed on an aligner and aligned to a precise position relative to a mask (within approximately 1-2 microns in the two horizontal dimensions and 10 microns in the vertical dimensions). The mask was designed to expose certain features on the wafer to UV light centered at 365 nm. The wafer was exposed through the mask for 7 seconds using a total exposure power of 19 milliwatts/cm$^2$. The wafer was again placed on the spin coater and 10 mL of methylisobutylketone was added while spinning at 2,000 RPM to remove the photoresist. This was followed by 10 mL of isopropanol at the same speed. 10 mL of a coupling solution consisting of Boc-Ser (0.1M), DIC (0.1M), and 6-Cl-HOBT (0.1M) in NMP was then added while spinning at 500 RPM. The wafer was then removed from the spin coater and a second clean wafer was placed on top of it in such a way that the coupling solution spun onto it was trapped between the two wafers. This arrangement was placed on a hot plate at 85° C. for 120 seconds. The cover plate was removed, the wafer placed back on the spin coater and 10 mL of NMP was added as the wafer was spun at 2,000 RPM to wash off the coupling solution. 10 mL of MIBK was then added as the wafer was spun at 2,000 RPM, followed by 10 mL IPA at the same speed to clean and dry the wafer.

Step (3) The process described above in (2) was repeated a number of times, each time using an appropriate mask and amino acid. The amino acids were added in the order: first=G; second=G; third=S; forth=G; fifth=G; sixth=S; seventh=G; eight=G; ninth=S; tenth=G; eleventh=G; twelfth=S; thirteenth=G; fourteenth=G; fifteenth=S; sixteenth=G; seventeenth=G; eighteenth=S; nineteenth=G; twentieth=G; twenty-first=S; twenty-second=G; twenty-third=V; twenty-fourth=V; twenty-fifth=S; twenty-six=H; twenty-seventh=R; twenty-eight=V; twenty-ninth=V; thirtieth=S; thirty-first=H; thirty-second=R; thirty-third=V; thirty-fourth=V; thirty-fifth=S; thirty-six=H; thirty-seventh=R; thirty-eighth=V; thirty-ninth=V; fortieth=S; fortieth-first=H; and fortieth-second=R. The masks were designed such that the number of G's and S's varied from one peptide to another, but all peptides ended with RHSVV (SEQ ID NO: 1) (the epitope for P53Ab1). All amino acids were added in the same concentration (0.1M) as shown in (2). The one letter designation of each amino acid is used in the foregoing and that designation is well known to those skilled in the art.

Step (4) The wafer described above was diced in such a way that the arrays of ~330,000 peptides could be individually exposed to specific samples as described previously (Legutki et al., 2014, Nature Communications, 5, Article number: 4785 doi:10.1038/ncomms5785). In this way arrays were incubated with 5.0 pM of a monoclonal antibody P53Ab1.

FIG. 2 illustrates the results of the surface stability test performed upon peptides synthesized successively on a seven amino acid linker. FIG. 2 illustrates a linker that was synthesized the surface and then RHSVV (SEQ ID NO: 1) was synthesized four times at different places. The production of the linker involved 24 synthetic cycles. The y-axis shows the intensity of binding of the P53Ab1 monoclonal antibody to RHSVV sequences (SEQ ID NO: 1) that were synthesized early in the synthesis (labeled RHSVVaGSG (SEQ ID NO: 7) in FIG. 2), and to sequences that were synthesized one cycle later (labeled RHSVVbGSG (SEQ ID NO: 7) in FIG. 2), two cycles later (labeled RHSVVcGSG (SEQ ID NO: 7) in FIG. 2), or three cycles later (labeled RHSVVdGSG (SEQ ID NO: 7) in FIG. 2). As illustrated in FIG. 2, the longer linker (GGGGGSG (SEQ ID NO: 5)) gives almost 10 times more P53Ab1 signal overall than the GSG linker (FIG. 1), which is a surprising and unexpected increase in binding strength considering the mere length difference of four amino acids. In addition, the change in binding as a function of when the epitope was made is minimal for peptides with the GGGGSG linker (SEQ ID NO: 4).

FIG. 3 illustrates the results of the surface stability test performed upon peptides synthesized successively on a three amino acid linker. The y-axis shows the intensity of binding of the P53Ab1 monoclonal antibody to RHSVV sequences (SEQ ID NO: 1) that were synthesized early in the synthesis (labeled RHSVVaGSG (SEQ ID NO: 7) in FIG. 3), and to sequences that were synthesized one cycle later (labeled RHSVVbGSG (SEQ ID NO: 7) in FIG. 3), two cycles later (labeled RHSVVcGSG (SEQ ID NO: 7) in FIG. 3), or three cycles later (labeled RHSVVdGSG (SEQ ID NO: 7) in FIG. 3). FIG. 4 illustrates that longer linkers result in high binding of the P53Ab1 to the surface.

Example 4: Application of the Immunosignature Approach to Detection and Identification of Infectious Disease Step (1). An 8 inch silicon wafer with a 2,500 angstrom thermal oxide layer was cleaned extensively with a solution of sulfuric acid (83.5% by volume) and 30% hydrogen peroxide (16.5% by volume). This surface was extensively flushed with highly purified water. The wafer was then placed in a 0.5% solution by volume of aminopropyltriethoxysilane in 95% ethanol and 4.5% water and allowed to sit without agitation for 90 minutes. The wafer was next washed in ethanol and isopropanol and placed in an oven at 110° C. for 90 minutes. Then the wafer was placed on a spin coater, and a 10 mL coupling solution of Boc-Gly (0.1M), 6-Cl-HOBT (0.1M), and diisopropylcarbodiimide (DIC, 0.1M) in N-methylpyrrolidinone (NMP) was added while spinning at 500 RPM. The wafer was then removed from the spin coater and a second clean wafer was placed on top of it in such a way that the coupling solution spun onto it was trapped between the two wafers. This arrangement was placed on a hot plate at 85° C. for 120 seconds. The cover plate was removed, the wafer placed back on the spin coater and 10 mL of NMP was added as the wafer was spun at 2,000 RPM to wash off the coupling solution. 10 mL of MIBK was then added as the wafer was spun at 2,000 RPM, followed by 10 mL IPA at the same speed to clean and dry the wafer. The coupling was repeated one more time.

Step (2). The wafer was placed on a spin coater and 10 mL of a photoresist solution (25 mg/ml poly methyl methacrylate (PMMA), 30 mg/ml Bis(4-t-butylphenyl)iodonium triflate (PAG) and 15 mg/mL isopropyl-9H-thioxanthen-9-one (ITX) in propylene glycol methyl ether acetate (PGMEA)) were added while spinning at 2,000 RPM. The wafer was then placed on a hot place at 75° C. for 1.5 minutes. The wafer was placed on an aligner and aligned to a precise position relative to a mask (within approximately 1-2 microns in the two horizontal dimensions and 10 microns in the vertical dimension). The mask was designed to expose certain features on the wafer is UV light centered at 365 nm. The wafer was exposed through the mask for 7 seconds using a total exposure power of 19 milliwatts/$cm^2$. The wafer was again placed on the spin coater and 10 mL of methylisobutylketone was added while spinning at 2,000 RPM to remove the photoresist. This was followed by 10 mL of isopropanol at the same speed. 10 mL of a coupling solution consisting of Boc-Ser (0.1M), DIC (0.1M), and 6-Cl-HOBT (0.1M) in NMP was then added while spinning at 500 RPM. The wafer was then removed from the spin coater and a second clean wafer was placed on top of it in such a way that the coupling solution spun onto it was trapped between the two wafers. This arrangement was placed on a hot plate at 85° C. for 120 seconds. The cover plate was removed, the wafer placed back on the spin coater and 10 mL of NMP was added as the wafer was spun at 2,000 RPM to wash off the coupling solution. 10 mL of MIBK was then added as the wafer was spun at 2,000 RPM, followed by 10 mL IPA at the same speed to clean and dry the wafer.

Step (3). The process described above in (2) was then repeated 18 times except that the mask alignment and light exposure were removed from the process. These are the conditioning steps of the overall procedure but with only one amino acid, Boc-Gly, used in the concentration of 0.1M as shown in (2).

Step (4). The wafer was then placed on a spin coater and 10 mL of a photoresist solution (25 mg/ml poly methyl methacrylate (PMMA), 30 mg/ml Bis(4-t-butylphenyl)iodonium triflate (PAG) and 15 mg/mL isopropyl-9Hthioxanthen-9-one (ITX) in propylene glycol methyl ether acetate (PGMEA)) were added while spinning at 2,000 RPM. The wafer was then placed on a hot place at 75° C. for 1.5 minutes. The wafer was placed on an aligner and aligned to a precise position relative to a mask (within approximately 1-2 microns in the two horizontal dimensions and 10 microns in the vertical dimension). The mask was designed to expose certain features on the wafer to UV light centered at 365 nm. The wafer was exposed through the mask for 7 seconds using a total exposure power of 19 milliwatts/cm$^2$. The wafer was again placed on the spin coater and 10 mL of MIBK was added while spinning at 2,000 RPM to remove the photoresist. This was followed by 10 mL of IPA at the same speed. 10 mL of a coupling solution consisting of Boc-Gly (0.1M), DIC (0.1M), and 6-Cl-HOBT (0.1M) in NMP was then added while spinning at 500 RPM. The wafer was then removed from the spin coater and a second clean wafer was placed on top of it in such a way that the coupling solution spun onto it was trapped between the two wafers. This arrangement was placed on a hot plate at 85° C. for 120 seconds. The cover plate was removed, the wafer placed back on the spin coater and 10 mL of NMP was added as the wafer was spun at 2,000 RPM to wash off the coupling solution. 10 mL of MIBK was then added as the wafer was spun at 2,000 RPM, followed by 10 mL IPA at the same speed.

Step (5). The process described above in (4) was repeated 69 times, each time using a different mask and a different amino acid. The amino acids were added in the order: first=G; second=G; third=G; fourth=R; fifth=L; sixth=Y; seventh=N; eight=H; ninth=S; tenth=D; eleventh=L; twelfth=W; thirteenth=K; fourteenth=E; fifteenth=H; sixteenth=K; seventeenth=W; eighteenth=D; nineteenth=V; twenty-first=Y; twenty-second=R; twenty-third=E; twenty-forth=F; twenty-fifth=P; twenty-sixth=V; twenty-seventh=F; twenty-eight=K; twenty-ninth; thirtieth=E; thirty-first=Q; thirty-second=N; thirty-third=Y; thirty-fourth=R; thirty-fifth=G; thirty-sixth=E; thirty-seventh=W; thirty-eight=D; thirty-ninth=G; fortieth=K; forty-first=Q; forty-second=L; forty-third; forty-fourth=Y; forty-fifth=V; forty-seventh=G; forty-eight=W; forty-ninth=E; fiftieth=G; fifty-first=S; fifty-second=P; fifty-third=R; fifty-fourth=V; fifty-fifth=P; fifty-sixth=H; fifty-seventh=R; fifty-eight=K; fifty-ninth=N; sixtieth=L; sixty-first=S; sixty-second=L; sixty-third=R; sixty-forth=A; sixty-fifth=D; sixty-eight=A; sixty-ninth=Y; seventieth=H; seventy-first=G; seventy-second=E; seventy-third=Q; seventy-forth=K; seventy-fifth=N). All amino acids were added in the same concentration of 0.1M. The one letter designation of each amino acid is used in the forgoing and that designation is well known to those skilled in the art.

Figure 5:
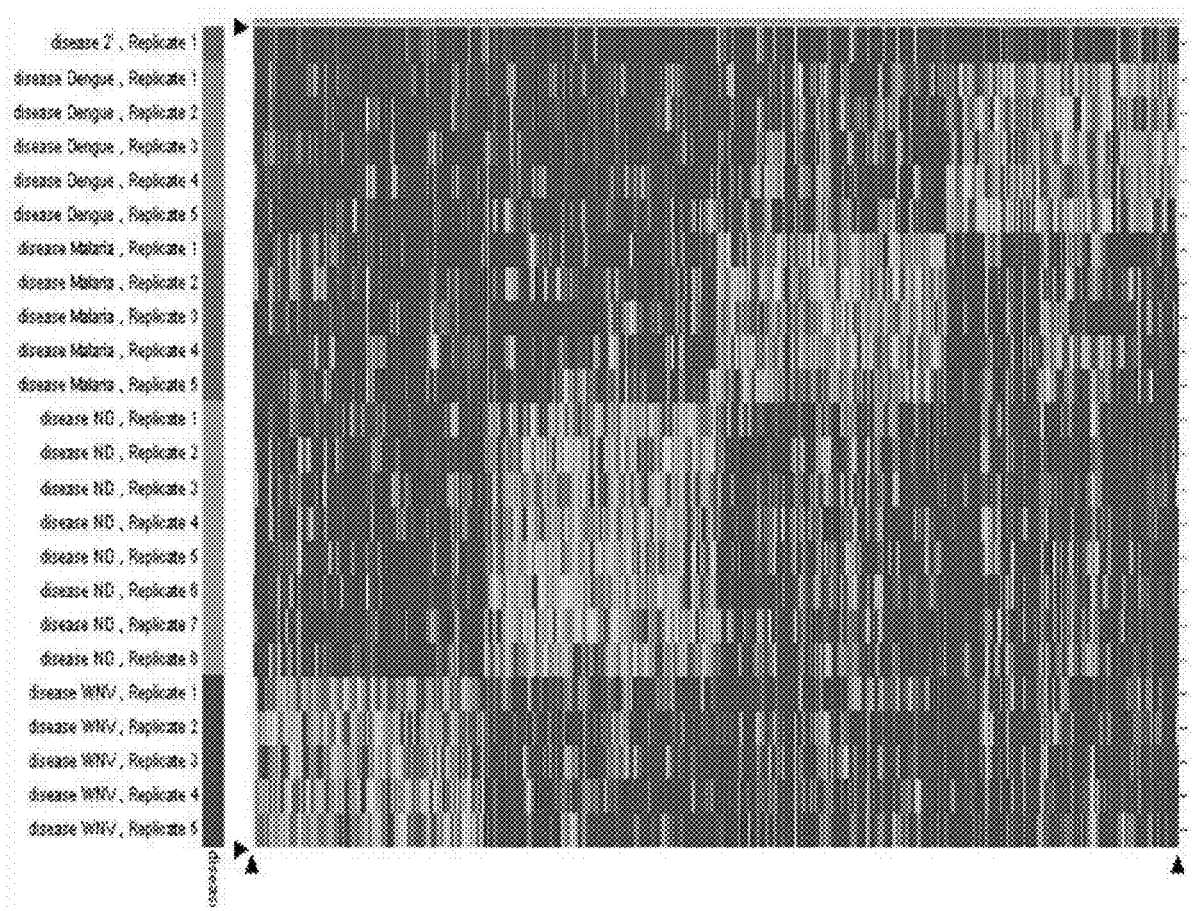

Step (6). The wafer described above was diced such that arrays of ~330,000 peptides could be individually exposed to specific samples as described previously. 24 blood samples from patients infected with Malaria, Dengue fever, West Nile Virus, or patients that were not infected were analyzed for binding patterns and the immunosignature was determined. A set of 50 peptides were chosen that provided the most unique antibody binding data for each of the diseases. See Legutki et al., *Nat. Commun.* 5:4785 (2014). FIG. 5 is a visual representation of an immunosignature as a heat map. Each column in the heat map represents a sample from an individual with a particular disease. Each row represents a peptide from the array. The color indicates the level of binding, with red being high binding and blue low binding. Note that for any particular disease, there is high binding only in a subset of peptides. That subset is distinct for different diseases.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An array, comprising:
   (a) a surface; and
   (b) a plurality of molecules immobilized to the surface; wherein the molecules comprise a peptide linker sequence having two ends, wherein one end of the peptide linker sequence is coupled to the surface and the other end is coupled to a functional sequence which binds a target molecule; and wherein the peptide linker sequence consists of GGSG, GGGSG, GGGGSG, GGGGGSG, or GGGGGGSG.

2. The array of claim 1, wherein the peptide linker sequence consists of GGGGGSG.

3. The array of claim 1, wherein the peptide linker sequence consists of GGGGGGSG.

4. An array, comprising:
   (a) a surface; and
   (b) a plurality of in situ synthesized molecules immobilized to the surface;
   wherein the molecules comprise a peptide linker sequence having two ends, wherein one end of the peptide linker sequence is coupled to the surface and the other end is coupled to a functional sequence which binds a target molecule; and wherein the peptide linker sequence consists of GGSG, GGGSG, GGGGSG, GGGGGSG, or GGGGGGSG.

5. The array of claim 4, wherein the peptide linker sequence consists of GGGGGSG.

6. The array of claim 4, wherein the peptide linker sequence consists of GGGGGGSG.

7. A method of making an array, comprising:
   (a) performing a chemical reaction upon the array that is capable of attaching an amino acid to a coupling site, wherein the amino acid forms part of a peptide linker sequence;
   (b) performing an additional chemical reaction upon the array that is capable of adding an amino acid to the attached amino acid of step (a); and
   (c) repeating step (b) at least once until the amino acids that comprise the desired peptide linker sequence have been added, wherein the desired peptide linker sequence consists of GGSG, GGGSG, GGGGSG, GGGGGSG, and GGGGGGSG;
   (d) synthesizing in situ a functional sequence onto the free end of the peptide linker sequence, wherein the peptide linker sequence enhances binding between the functional sequence and a substrate.

8. The method of claim 7, wherein the peptide linker sequence length consists of GGGGGSG.

* * * * *

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg His Ser Val Val
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Gly Gly Ser Gly
1

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Ser Gly
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Gly Gly Ser Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Gly Gly Gly Ser Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Gly Gly Gly Gly Ser Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg His Ser Val Val Gly Ser Gly
1               5

<210> SEQ ID NO 8
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 8

Arg His Ser Val Val Gly Gly Gly Gly Ser Gly
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg His Ser Val Val Gly Gly Ser Gly
1               5

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg His Ser Val Val Gly Gly Gly Ser Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg His Ser Val Val Gly Gly Gly Gly Ser Gly
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg His Ser Val Val Gly Gly Gly Gly Gly Gly Ser Gly
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg His Ser Val Val Gly Gly Gly Gly Gly Gly Gly Ser Gly
1               5                   10
```

```
<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Gly Gly Gly Gly Gly Gly Ser Gly
1               5
```